(12) United States Patent
Singh et al.

(10) Patent No.: US 8,669,230 B2
(45) Date of Patent: Mar. 11, 2014

(54) IMMUNOGENIC EPITOPES FOR IMMUNOTHERAPY

(75) Inventors: Harpreet Singh, Tubingen (DE); Steffen Walter, Dusslingen (DE); Toni Weinschenk, Aichwald (DE); Norbert Hilf, Kirchentellinsfurt (DE); Oliver Schoor, Tubingen (DE); Claudia Lemmel, Wuelfrath (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 596 days.

(21) Appl. No.: 12/915,473

(22) Filed: Oct. 29, 2010

(65) Prior Publication Data

US 2011/0117117 A1    May 19, 2011

Related U.S. Application Data

(62) Division of application No. 12/180,045, filed on Jul. 25, 2008, now Pat. No. 8,080,634.

(60) Provisional application No. 60/953,161, filed on Jul. 31, 2007.

(30) Foreign Application Priority Data

Jul. 27, 2007 (EP) .................................. 07014797

(51) Int. Cl.
*C07K 7/00* (2006.01)

(52) U.S. Cl.
USPC .......... 514/19.2; 530/328; 530/324; 530/325; 530/326; 530/327

(58) Field of Classification Search
None
See application file for complete search history.

(56) References Cited

U.S. PATENT DOCUMENTS

| | | | |
|---|---|---|---|
| 6,531,447 B1 | 3/2003 | Ruben et al. | |
| 7,396,904 B2 | 7/2008 | Weinschenk et al. | |
| 2002/0048763 A1* | 4/2002 | Penn et al. | 435/6 |
| 2006/0123505 A1* | 6/2006 | Kikuchi et al. | 800/278 |

FOREIGN PATENT DOCUMENTS

| | | |
|---|---|---|
| WO | 01/54733 | 8/2001 |
| WO | 02/059609 | 8/2002 |
| WO | 2002078524 | 10/2002 |
| WO | 2003000113 | 1/2003 |
| WO | 2004030615 | 4/2004 |
| WO | 2005044990 | 5/2005 |
| WO | 2005116051 | 12/2005 |
| WO | 2007028574 | 3/2007 |

OTHER PUBLICATIONS

McDevitt H., "Specific antigen vaccination to treat autoimmune disease," PNAS, Oct. 5, 2004, vol. 101, pp. 14627-14630.

Mihalyo et al., "In Vivo Cyclophosphamide and IL-2 Treatment Impedes Self-Antigen-Induced Effector CD4 Cell Tolerization: Implications for Adoptive Immunotherapy," J. Immunol, 2004, pp. 5338-5345.
Oehlen et al., "Expression of a Tolerizing Tumor Antigen in Peripheral Tissue Does Not Preclude of High-Affinity CD8+ T Cells or CTL Immunotherapy of Tumors Expressing the Antigen," J. Immunol, 2001, pp. 2863-2870.
Adler A., "Peripheral Tolerization of Effector and Memory T Cells: Implications for Autoimmunity and Tumor-Immunity," Curr Immunol Rev., Jan. 1, 2005, 1(1) pp. 21-28.
Vella et al., "B cells are not essential for peripheral T-cell tolerance," Poc. Natl. Acad. Sci, Jan. 1996, vol. 93, pp. 951-955.
Vidard et al., "Specific T-cell tolerance may be preceded by a primary response," Proc. Natl. Acad. Sci., Jun. 1994, vol. 91, pp. 5627-5631.
Sadovnikova et al., "Peptide-specific cytotoxic T lymphocytes restricted by nonself major histocompatibility complex class I molecules: Reagents for tumor immunotherapy," Proc. Natl. Acad. Sci., Nov. 1996, vol. 93, pp. 13114-13118.
Kurts et al., "CD8 T cell ignorance or tolerance to islet antigens depends on antigen dose," PNAS, Oct. 26, 1999, vol. 96, No. 22, pp. 12703-12707.
Polymenidou et al., "Humoral immune response to native eukaryotic prion protein correlates with anti-prion protection," PNAS, Oct. 5, 2004, vol. 101, pp. 14670-14676.
Maeda et al., "Supressor T cells regulate the nonanergic cell population that remains after peripheral tolerance is induced . . . ," PNAS, Nov. 21, 2000, vol. 97, No. 24, pp. 13257-13262.
"Approved Drugs for Oncology," Center Watch: Oncology Approved Drug Therapies, retrieved from the WWW on Sep. 10, 2010, pp. 1-8 (http://www.centerwatch.com/drug-information/fda-approvals/drug-areas.aspx?AreaID=12).
A search of the National Institutes of Health's ("NIH") clinicaltrials.gov website on Aug. 23, 2010 for the terms "cancer" AND "peptide vaccine" discloses 74 clinical trials that were first received by the NIH between Jan. 1, 1996 and Jul. 27, 2007.
"FDA Approves PROVENGE(R) for the Treatment of Men with Advanced Prostate Cancer," Dendreon Press Release, Apr. 29, 2010, pp. 1-3.
Data from the NIH's clinicaltrials.gov website, clinical trials for Provenge®, 2001.
Ezzell, C., "Cancer "Vaccines": An Idea Whose Time Has Come?", The Journal of NIH Research, Jan. 1995, vol. 7, pp. 46-49.
Spitler et al., "Cancer Vaccines: The Interferon Analogy," Cancer Biotherapy, 1995, vol. 10, No. 1, pp. 1-3, Mary Ann Liebert, Inc.
Boon, T., "Toward a Genetic Analysis of Tumor Rejection Antigens," Adv. Can. Res., 1992, col. 58, pp. 177-210.

(Continued)

*Primary Examiner* — Sheela J Huff
(74) *Attorney, Agent, or Firm* — Miles & Stockbridge, P.C.

(57) ABSTRACT

The present invention relates to peptides, nucleic acids and cells for use in immunotherapeutic methods. In particular, the present invention relates to the immunotherapy of cancer. The present invention furthermore relates to tumor-associated T-helper cell peptide epitopes, alone or in combination with other tumor-associated peptides that serve as active pharmaceutical ingredients of vaccine compositions which stimulate anti-tumor immune responses. The present invention relates to novel peptide sequences and their variants derived from HLA class I and class II molecules of human tumor cells which can be used in vaccine compositions for eliciting anti-tumor immune responses.

14 Claims, 23 Drawing Sheets

(56) References Cited

OTHER PUBLICATIONS

Freshney, I., "Culture of Animal Cells, A Manual of Basic Technique," 1983, pp. 3-4, Alan R. Liss, Inc., New York.
Dermer, G., "Another Anniversary for the War on Cancer," Bio/Technology, Mar. 1994, vol. 12, p. 320.
Gura, T., "Systems for Identifying New Drugs Are Often Faulty," Science, Nov. 7, 1997, vol. 278, pp. 1041-1042.
Jain, R., "Barriers to Drug Delivery in Solid Tumors," Scientific American, Jul. 1994, vol. 271, No. 1, pp. 58-65.
Database GENESEQ [Online] Nov. 7, 2001, "Novel Signal Transduction Pathway Protein, SEQ ID 642." XP002497882 Retrieved From EBI Accession No. GSP: AAU17077 Database Accession No. AAU17077, The Whole Document.
Database UNIPROT [Online] Sep. 13, 2005, "Subname: Full=FERMT1 PROTEI;" XP002497883, Retrieved From EBI Accession No. UNIPROT; Q49AC8, Database Accession No. Q49AC8, The Whole Document.
Database GENESEQ [Online], Sep. 3, 2001, "Human Colon Cancer Antigen Protein SEQ ID No. 6503." XP002505842, Retrieved From EBI Accession No. GSP: AAG75739, Database Accession No. AAG75739, The Whole Document.
Database UNIPROT [Online], May 1, 2000, "Recname: Full=NADPH Oxidase 1; Short=NOX-1; EC=<A HREF=" http://srs.ebi.ac.uk/srsbin/cgi-bin/wgetz?[enzyme-ecnumber;1.*.*.*]+-E>1.-.-.-</A>; Altname: Full=NOH-1; Alt Name; Full=NADH/NADPH Mitogenic Oxidase Subunit P65-MOX; Altname; Full=Mitogenic Oxidase1; Short=MOX1; XP002505848, Retrieved From EBI Accession No. UNIPROT: Q9Y5S8 Database Accession No. Q9Y5S8, The Whole Document.
Database GENESEQ [Online], Jan. 29, 2003, "Human Expressed Protein Tag (EPT) #29." XP002505843 Retrieved From EBI Accession No. GSP: ABU03249, Database Accesion No. ABU03249 Discloses Sequence 29 of WO02078524. The Whole Document.
Database UNIPROT [Online] Oct. 1, 1989, "Recname: Full=Proliferating Cell Nuclear Antigen; Short=PCNA; Altname: Full=Cyclin;" XP002505844, Retrieved From EBI Accession No. UNIPROT: p12004, Database Accession No. P12004, Comprises Present Sequence 3. The Whole Document.
Database GENESEQ [Online], Nov. 14, 2004, "Tumour-Associated Antigenic Target (TAT) Polypeptide PR080966, SEQ: 1080." XP002505845, Retrieved From EBI Accession No. GSP: ABM80429. Database Accession No. ABM80429 Discloses Sequence 1080 of WO2004030615. The Whole Document.
Database UNIPROT [Online], Jul. 1, 1993, "Recname: Full-DNA Topoisomerase 2-Beta; EC=<A HREF="http:/srs.ebi.sc.uk/srsbin/cgi-bin/wgetz?[enzyme-ecnumber:5.99.1.3</a>; Altname: Full=DNA Topoisomerase II, Beta Isozyme; XP002505846, Retrieved From EBI Accession No. UNIPROT:Q02880 Database Accession No. Q02880. The Whole Document.
Database UNIPROT [Online], "Recname: Full-DNA Topoisomerase 2-Alpha; EC=<A HREF="http://srs.ebi.sc.uk/srsbin/cgi-bin/wgetz?enzyme-ecnumber:5.99.1.3]+-E">5.99.1.3.</a>; Altname: Full=DNA Topoisomerase II, Alpha Isozyme;" XP002505847, Retrieved From EBI Accession No. UNIPROT P11388; Database Accession No. P11388. The Whole Document, (1989).
Search Report for PCT/EP2008/006153; Dated Jan. 19, 2009.
Written Opinion of PCT/EP2008/008153 Dated Aug. 21, 2009,.
Database UNIPROT [Online]: Q4TE8O-TETNG, "Full=Chromosome Undertermined SCAF5582, Whole Genome Shotgun Sequence", Jul. 19, 2005. Whitehead Institute Center for Genome Research.
Database GENESEQP [ONLINE]:ABP64001, Leach, MD et al. "New Polypeptide Designated ORFX Are Present in Human Atherogenic Cells and Are Useful to Preven and Treat OFRX-Associated Disorders Including Cancer, Allergy, Wouldn Healing or Autoimmune, Cardiovascular or Inflammatory Disease" Nov. 4, 2002.
Fikes, J., Ph.D, The Rational Design of T-Cell Epitopes With Enhanced Immunogenicity, Handbook of Cancer Vaccines, pp. 11-17 (edits by Morse, M.A. et al. 2004).
Fong, L, et al., Proc. Natl. Acad. Sci. U.S.A, vol. 98, No. 15, pp. 8809-8814 (2001).
Topalian, S. L. et al., Cancer Immunotherapy Comes of Age, Journal of Clinical Oncology, vol. 29, No. 36, pp. 4828-4836 (Dec. 20, 2011).
Walter, S. et al., In vitro veritas: Successful in vitro prediction of clinical immunogenicity of two cancer vaccines, Abstract No. 753, American Association for Cancer Research Annual Meeting (Apr. 2011).

* cited by examiner

SEQUENCE LISTING

<160> NUMBER OF SEQ ID NOS: 44

<210> SEQ ID NO 1
<211> LENGTH: 9
<212> TYPE: PRT
<213> ORGANISM: Homo sapiens

<400> SEQUENCE: 1

Ala Leu Ser Asn Leu Glu Val Thr Leu
1               5

<210> SEQ ID NO 2
<211> LENGTH: 9
<212> TYPE: PRT
<213> ORGANISM: Homo sapiens

<400> SEQUENCE: 2

Ile Leu Ala Pro Val Ile Leu Tyr Ile
1               5

<210> SEQ ID NO 3
<211> LENGTH: 10
<212> TYPE: PRT
<213> ORGANISM: Homo sapiens

<400> SEQUENCE: 3

```
Lys Leu Met Asp Leu Asp Val Glu Gln Leu
1               5                   10

<210> SEQ ID NO 4
<211> LENGTH: 9
<212> TYPE: PRT
<213> ORGANISM: Homo sapiens

<400> SEQUENCE: 4

Ser Met Ser Ala Asp Val Pro Leu Val
1               5

<210> SEQ ID NO 5
<211> LENGTH: 10
<212> TYPE: PRT
<213> ORGANISM: Homo sapiens

<400> SEQUENCE: 5

Lys Ile Phe Asp Glu Ile Leu Val Asn Ala
1               5                   10

<210> SEQ ID NO 6
<211> LENGTH: 10
<212> TYPE: PRT
<213> ORGANISM: Homo sapiens

<400> SEQUENCE: 6

Ala Ala Phe Val Glu Glu Leu Asp Lys Val
1               5                   10

<210> SEQ ID NO 7
<211> LENGTH: 14
<212> TYPE: PRT
<213> ORGANISM: Homo sapiens

<400> SEQUENCE: 7

Val Leu Leu Leu Val His Asn Leu Pro Gln His Leu Phe Gly
1               5                   10

<210> SEQ ID NO 8
<211> LENGTH: 10
<212> TYPE: PRT
<213> ORGANISM: Homo sapiens

<400> SEQUENCE: 8

Ala Leu Phe Val Arg Leu Leu Ala Leu Ala
1               5                   10

<210> SEQ ID NO 9
<211> LENGTH: 14
<212> TYPE: PRT
<213> ORGANISM: Homo sapiens

<400> SEQUENCE: 9

Gly Asp Lys Leu Glu Val Ser Leu Lys Asn Asn Val Val Ser
1               5                   10

<210> SEQ ID NO 10
<211> LENGTH: 18
<212> TYPE: PRT
<213> ORGANISM: Homo sapiens

<400> SEQUENCE: 10

Gly Lys Lys Leu Arg Val Phe Val Tyr Arg Asn Ser Leu Cys Ile Glu
1               5                   10                  15
```

Asn Ser

<210> SEQ ID NO 11
<211> LENGTH: 17
<212> TYPE: PRT
<213> ORGANISM: Homo sapiens

<400> SEQUENCE: 11

Leu Lys Asn Asn Val Val Ser Val Asn Lys Glu Pro Val Ala Glu Pro
1               5                   10                  15

Asp

<210> SEQ ID NO 12
<211> LENGTH: 15
<212> TYPE: PRT
<213> ORGANISM: Homo sapiens

<400> SEQUENCE: 12

Asn Gly Val Ile His Tyr Ile Asp Glu Leu Leu Ile Pro Asp Ser
1               5                   10                  15

<210> SEQ ID NO 13
<211> LENGTH: 14
<212> TYPE: PRT
<213> ORGANISM: Homo sapiens

<400> SEQUENCE: 13

Leu Asn Arg Ile Leu Gly Asp Pro Glu Ala Leu Arg Asp Leu
1               5                   10

<210> SEQ ID NO 14
<211> LENGTH: 15
<212> TYPE: PRT
<213> ORGANISM: Homo sapiens

<400> SEQUENCE: 14

Thr Pro Pro Ile Asp Ala His Thr Arg Asn Leu Leu Arg Asn His
1               5                   10                  15

<210> SEQ ID NO 15
<211> LENGTH: 9
<212> TYPE: PRT
<213> ORGANISM: Homo sapiens

<400> SEQUENCE: 15

Ala Leu Thr Thr Leu Met His Gln Leu
1               5

<210> SEQ ID NO 16
<211> LENGTH: 9
<212> TYPE: PRT
<213> ORGANISM: Homo sapiens

<400> SEQUENCE: 16

Ser Leu Asp Pro Ser Ser Pro Gln Val
1               5

<210> SEQ ID NO 17
<211> LENGTH: 9
<212> TYPE: PRT
<213> ORGANISM: Homo sapiens

<400> SEQUENCE: 17

Ser Leu Trp Ala Gly Val Val Val Leu
1               5

<210> SEQ ID NO 18
<211> LENGTH: 9
<212> TYPE: PRT
<213> ORGANISM: Homo sapiens

<400> SEQUENCE: 18

Lys Leu Thr Asp Ile Gln Ile Glu Leu
1               5

<210> SEQ ID NO 19
<211> LENGTH: 9
<212> TYPE: PRT
<213> ORGANISM: Homo sapiens

<400> SEQUENCE: 19

Tyr Leu Ile His Phe Pro Val Ser Val
1               5

<210> SEQ ID NO 20
<211> LENGTH: 9
<212> TYPE: PRT
<213> ORGANISM: Homo sapiens

<400> SEQUENCE: 20

Ile Val Asp Asp Ile Thr Tyr Asn Val
1               5

<210> SEQ ID NO 21
<211> LENGTH: 16
<212> TYPE: PRT
<213> ORGANISM: Homo sapiens

<400> SEQUENCE: 21

Gly Ala Val Arg Phe Ser Asn Asn Pro Ala Leu Cys Asn Val Glu Ser
1               5                   10                  15

<210> SEQ ID NO 22
<211> LENGTH: 16
<212> TYPE: PRT
<213> ORGANISM: Homo sapiens

<400> SEQUENCE: 22

Asn Pro Thr Thr Tyr Gln Met Asp Val Asn Pro Glu Gly Lys Tyr Ser
1               5                   10                  15

<210> SEQ ID NO 23
<211> LENGTH: 13
<212> TYPE: PRT
<213> ORGANISM: Homo sapiens

<400> SEQUENCE: 23

Phe Lys Lys Ile Lys Val Leu Gly Ser Gly Ala Phe Gly
1               5                   10

<210> SEQ ID NO 24
<211> LENGTH: 18
<212> TYPE: PRT
<213> ORGANISM: Homo sapiens

<400> SEQUENCE: 24

Thr Thr Leu Ile Lys Glu Met Lys Ala Glu Phe Ile Lys Glu Ala Gln
1               5                   10                  15

Pro Gly

```
<210> SEQ ID NO 25
<211> LENGTH: 15
<212> TYPE: PRT
<213> ORGANISM: Homo sapiens

<400> SEQUENCE: 25

Val Lys Ser Lys Val Gln Tyr Leu Lys Asp Arg Gln Leu Ala Gly
1               5                   10                  15

<210> SEQ ID NO 26
<211> LENGTH: 15
<212> TYPE: PRT
<213> ORGANISM: Homo sapiens

<400> SEQUENCE: 26

Ser Arg Arg Thr Phe Ile Lys Ser Val Pro Pro Phe Leu Arg Thr
1               5                   10                  15

<210> SEQ ID NO 27
<211> LENGTH: 11
<212> TYPE: PRT
<213> ORGANISM: Homo sapiens

<400> SEQUENCE: 27

Lys Leu Gly Asp Phe Gly Leu Ala Thr Val Val
1               5                   10

<210> SEQ ID NO 28
<211> LENGTH: 9
<212> TYPE: PRT
<213> ORGANISM: Homo sapiens

<400> SEQUENCE: 28

Ser Leu Phe Asp Gln Val Val Lys Val
1               5

<210> SEQ ID NO 29
<211> LENGTH: 9
<212> TYPE: PRT
<213> ORGANISM: Homo sapiens

<400> SEQUENCE: 29

Ala Leu Leu Ser Glu Val Ile Gln Leu
1               5

<210> SEQ ID NO 30
<211> LENGTH: 16
<212> TYPE: PRT
<213> ORGANISM: Homo sapiens

<400> SEQUENCE: 30

Lys Asn Asn Val Val Ser Val Asn Lys Glu Pro Val Ala Glu Pro Asp
1               5                   10                  15

<210> SEQ ID NO 31
<211> LENGTH: 13
<212> TYPE: PRT
<213> ORGANISM: Homo sapiens

<400> SEQUENCE: 31

Lys Asn Asn Val Val Ser Val Asn Lys Glu Pro Val Ala
1               5                   10

<210> SEQ ID NO 32
<211> LENGTH: 14
```

```
<212> TYPE: PRT
<213> ORGANISM: Homo sapiens

<400> SEQUENCE: 32

Leu Lys Asn Asn Val Val Ser Val Asn Lys Glu Pro Val Ala
1               5                   10

<210> SEQ ID NO 33
<211> LENGTH: 15
<212> TYPE: PRT
<213> ORGANISM: Homo sapiens

<400> SEQUENCE: 33

Gly Val Ile His Tyr Ile Asp Glu Leu Leu Ile Pro Asp Ser Ala
1               5                   10                  15

<210> SEQ ID NO 34
<211> LENGTH: 15
<212> TYPE: PRT
<213> ORGANISM: Homo sapiens

<400> SEQUENCE: 34

Ala Val Arg Phe Ser Asn Asn Pro Ala Leu Cys Asn Val Glu Ser
1               5                   10                  15

<210> SEQ ID NO 35
<211> LENGTH: 14
<212> TYPE: PRT
<213> ORGANISM: Homo sapiens

<400> SEQUENCE: 35

Ala Val Arg Phe Ser Asn Asn Pro Ala Leu Cys Asn Val Glu
1               5                   10

<210> SEQ ID NO 36
<211> LENGTH: 17
<212> TYPE: PRT
<213> ORGANISM: Homo sapiens

<400> SEQUENCE: 36

Thr Leu Ile Lys Glu Met Lys Ala Glu Phe Ile Lys Glu Ala Gln Pro
1               5                   10                  15
Gly

<210> SEQ ID NO 37
<211> LENGTH: 15
<212> TYPE: PRT
<213> ORGANISM: Homo sapiens

<400> SEQUENCE: 37

Thr Thr Leu Ile Lys Glu Met Lys Ala Glu Phe Ile Lys Glu Ala
1               5                   10                  15

<210> SEQ ID NO 38
<211> LENGTH: 14
<212> TYPE: PRT
<213> ORGANISM: Homo sapiens

<400> SEQUENCE: 38

Thr Leu Ile Lys Glu Met Lys Ala Glu Phe Ile Lys Glu Ala
1               5                   10

<210> SEQ ID NO 39
<211> LENGTH: 15
<212> TYPE: PRT
```

```
<213> ORGANISM: Homo sapiens

<400> SEQUENCE: 39

Ile Lys Glu Met Lys Ala Glu Phe Ile Lys Glu Ala Gln Pro Gly
1               5                   10                  15

<210> SEQ ID NO 40
<211> LENGTH: 14
<212> TYPE: PRT
<213> ORGANISM: Homo sapiens

<400> SEQUENCE: 40

Thr Thr Leu Ile Lys Glu Met Lys Ala Glu Phe Ile Lys Glu
1               5                   10

<210> SEQ ID NO 41
<211> LENGTH: 8
<212> TYPE: PRT
<213> ORGANISM: Homo sapiens

<400> SEQUENCE: 41

Tyr Thr Ile Tyr Val Ile Ala Leu
1               5

<210> SEQ ID NO 42
<211> LENGTH: 9
<212> TYPE: PRT
<213> ORGANISM: Homo sapiens

<400> SEQUENCE: 42

Tyr Leu Leu Pro Ala Ile Val His Ile
1               5

<210> SEQ ID NO 43
<211> LENGTH: 10
<212> TYPE: PRT
<213> ORGANISM: Homo sapiens

<400> SEQUENCE: 43

Glu Leu Ala Gly Ile Gly Ile Leu Thr Val
1               5                   10

<210> SEQ ID NO 44
<211> LENGTH: 10
<212> TYPE: PRT
<213> ORGANISM: Homo sapiens

<400> SEQUENCE: 44

Phe Leu Pro Ser Asp Phe Phe Pro Ser Val
1               5                   10
```

IMMUNOGENIC EPITOPES FOR IMMUNOTHERAPY

RELATED APPLICATIONS

This application is a divisional of U.S. application Ser. No. 12/180,045, filed on Jul. 25, 2008 and claims priority to European application number EP07014797.0, filed on Jul. 27, 2007 and U.S. Provisional application 60/953,161, filed on Jul. 31, 2007 which are both incorporated by reference in their entirety. For the purposes of the present invention, all references as cited herein are incorporated by reference in their entireties.

FIELD OF THE INVENTION

The present invention relates to novel amino acid sequences of peptides derived from tumour associated antigens that are able to bind to MHC complexes of either class, and elicit an immune response.

BACKGROUND OF THE INVENTION

Stimulation of an immune response is dependent upon the presence of antigens recognised as foreign by the host immune system. The discovery of the existence of tumour associated antigens has now raised the possibility of using a host's immune system to intervene in tumour growth. Various mechanisms of harnessing both the humoral and cellular arms of the immune system are currently being explored for cancer immunotherapy.

Certain elements of the cellular immune response are capable of specifically recognising and destroying tumour cells. The isolation of cytotoxic T-cells (CTL) from tumour-infiltrating cell populations or from peripheral blood suggests that these cells play an important role in natural immune defences against cancer (Cheever et al., Annals N.Y. Acad. Sci. 1993 690:101-112; Zeh H J, et al.; J. Immunol. 1999, 162(2):989-94). CD8-positive T-cells (TCD8$^+$) in particular, which recognise Class I molecules of the major histocompatibility complex (MHC)-bearing peptides of usually 8 to 10 amino acid residues derived from proteins or defect ribosomal products (DRIPS) (Schubert U, et al., Nature 2000; 404 (6779):770-774) located in the cytosol, play an important role in this response. The MHC-molecules of a human are also designated as human leukocyte-antigens (HLA).

There are two classes of MHC-molecules: MHC class I molecules that can be found on most cells having a nucleus that present peptides that result from proteolytic cleavage of endogenous proteins, DRIPS, and larger peptides. MHC class II molecules can be found predominantly on professional antigen presenting cells (APCs), and present peptides of exogenous proteins that are taken up by APCs during the course of endocytosis, and are subsequently processed (Cresswell P., Annu Rev. Immunol. 1994; 12:259-93). Complexes of peptide and MHC class I molecules are recognised by CD8-positive cytotoxic T-lymphocytes bearing the appropriate TCR, and complexes of peptide and MHC class II molecules are recognised by CD4-positive-helper-T-cells bearing the appropriate TCR. It is well known that the TCR, the peptide and the MHC are thereby abundant in a stoichiometric amount of 1:1:1.

CD4-positive helper T-cells play an important role in orchestrating the effector functions of anti-tumour T-cell responses. For this reason, the identification of CD4-positive T-cell epitopes derived from tumour associated antigens (TAA) may be of great importance for the development of pharmaceutical products for triggering anti-tumour immune responses (Kobayashi, H., et al., 2002. Clin. Cancer Res. 8:3219-3225; Gnjatic, S., et al., 2003. Proc. Natl. Acad. Sci. U.S.A. 100(15):8862-7). CD4+ T cells can lead to locally increased levels of IFNγ, a critical requirement of interferon gamma-mediated angiostasis for tumour rejection by CD8+ T cells (Qin Z, et al., Cancer Res. 2003 J; 63(14):4095-4100).

In the absence of inflammation, expression of MHC class II molecules is mainly restricted to cells of the immune system, especially professional antigen-presenting cells (APC), e.g., monocytes, monocyte-derived cells, macrophages, dendritic cells. In tumour patients, cells of the tumour have surprisingly been found to express MHC class II molecules (Dengjel J, et al., Clin Cancer Res. 2006; 12:4163-4170).

It was shown in mammalian animal models, e.g., mice, that even in the absence of CTL effector cells (i.e., CD8-positive T lymphocytes), CD4-positive T-cells are sufficient for inhibiting visualization of tumours via inhibition of angiogenesis by secretion of interferon-gamma (IFNγ) (Qin, Z. et al., 2000. Immunity. 12:677-686). Additionally, it was shown that CD4-positive T-cells recognizing peptides from tumour-associated antigens presented by HLA class II molecules can counteract tumour progression via the induction of antibody (Ab) responses (Kennedy, R. C., et al., Cancer Res. 63:1040-1045). In contrast to tumour-associated peptides binding to HLA class I molecules, only a small number of class II ligands of TAA have been described so far. See generally, the syfpeithi database listing known MHC ligands and peptide motifs and Cancer Immunity, the Journal of Academy of Cancer Immunology.

Since the constitutive expression of HLA class II molecules is usually limited to cells of the immune system (Mach, B., et al., 1996. Annu Rev. Immunol. 14:301-331), the possibility of isolating class II peptides directly from primary tumours was not considered possible. However, Dengjel et al. were recently successful in identifying a number of MHC Class II epitopes directly from tumours (See EP 04 023 546.7, EP 05 019 254.1; Dengjel J, et al., Clin Cancer Res. 2006; 12:4163-4170).

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-10 amino acid residues in length and usually contain two conserved residues ("anchors") in their sequence that interact with the corresponding binding groove of the MHC-molecule. In this way each MHC allele has a "binding motif" determining which peptides can bind specifically to the binding groove (Rammensee H. G., et al, Chapman & 1998 Hall MHC Ligands and Peptide Motifs).

In the MHC class I dependent immune reaction, peptides not only have to be able to bind to certain MHC class 1 molecules expressed by tumour cells, they also have to be recognized by T-cells bearing specific T-cell receptors (TCR).

The antigens that are recognised by the tumour specific cytotoxic T-lymphocytes, that is, their epitopes, can be molecules derived from all protein classes, such as enzymes, receptors, transcription factors, etc., which are up-regulated in cells of the respective tumour. Furthermore, tumour associated antigens, for example, can also be unique to tumour cells, for example as products of mutated genes or from alternative open reading frames (ORFs), or from protein splicing (Vigneron N, et al., Science 2004 Apr. 23; 304 (5670):587-90). Another important class of tumour associated antigens are tissue-specific antigens, such as CT ("cancer testis")-antigens that are expressed in different kinds of tumours and in healthy tissue of the testis.

Various tumour associated antigens have been identified. Further, much research effort has been spent to identify additional tumour associated antigens. Some groups of tumour associated antigens, also referred to in the art as tumour specific antigens, are tissue specific. Examples include, but are not limited to, tyrosinase for melanoma, PSA and PSMA for prostate cancer and chromosomal cross-overs such as bcr/abl in lymphomas. However, many tumour associated antigens identified to date occur in multiple tumour types, and some, such as oncogenic proteins and/or tumour suppressor genes (tumour suppressor genes are, for example reviewed for renal cancer in Linehan W M, et al., J. Urol. 2003 December; 170(6 Pt 1): 2163-72), which actually cause the transformation event, occur in nearly all tumour types. For example, normal cellular proteins that control cell growth and differentiation, such as p53 (which is an example for a tumour suppressor gene), ras, c-met, myc, pRB, VHL, and HER-2/neu, can accumulate mutations resulting in up-regulation of expression of these gene products thereby making them oncogenic (McCartey et al. Cancer Research 1998 15:58 2601-5; Disis et al. Ciba Found. Symp. 1994 187:198-211). These mutant proteins can also be a target of a tumour specific immune response in multiple types of cancer.

For proteins to be recognised by cytotoxic T-lymphocytes as tumour-specific or -associated antigens, and for them to be used in a therapy, particular prerequisites must be fulfilled. The antigen should be expressed mainly by tumour cells and not, or in comparably small amounts, by normal healthy tissues. It is furthermore desirable, that the respective antigen is not only present in a type of tumour, but also in high concentrations (i.e. copy numbers of the respective peptide per cell). Tumour-specific and tumour-associated antigens are often derived from proteins directly involved in transformation of a normal cell to a tumour cell due to a function e.g. in cell cycle control or apoptosis. Additionally, downstream targets of the proteins directly causative for a transformation may be upregulated and thus may be indirectly tumour-associated. Such indirectly tumour-associated antigens may also be targets of a vaccination approach (Singh-Jasuja H., et al., Cancer Immunol. Immunoether. 2004 March; 453 (3): 187-95). In both cases it is essential to have epitopes in the amino acid sequence of the antigen, since such peptide ("immunogenic peptide") that is derived from a tumour associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T-cell with a corresponding TCR and the absence of immunological tolerance for this particular epitope.

Therefore, TAAs are a starting point for the development of a tumour vaccine. The methods for identifying and characterizing the TAAs are based on the use of CTL that can be isolated from patients or healthy subjects, or they are based on the generation of differential transcription profiles or differential peptide expression patterns between tumours and normal tissues (Lemmel C., et al., Nat. Biotechnol. 2004 April; 22(4):450-4; T. Weinschenk, et al., Cancer Res. 62 (20):5818-5827, 2002.).

However, the identification of genes overexpressed in tumour tissues or human tumour cell lines, or selectively expressed in such tissues or cell lines, does not provide precise information as to the use of the antigens transcribed from these genes in an immune therapy. This is because only an individual subpopulation of epitopes of these antigens are suitable for such an application since a T-cell with a corresponding TCR has to be present and immunological tolerance for this particular epitope needs to be absent or minimal. It is therefore important to select only those peptides from overexpressed or selectively expressed proteins that are presented in connection with MHC molecules against which a functional T-cell can be found. Such a functional T-cell is defined as a T-cell that upon stimulation with a specific antigen can be clonally expanded and is able to execute effector functions ("effector T-cell").

T-helper cells play an important role in orchestrating the effector function of CTLs in anti-tumour immunity. T-helper cell epitopes that trigger a T-helper cell response of the $T_{H1}$ type support effector functions of CD8-positive killer T-cells, which include cytotoxic functions directed against tumour cells displaying tumour-associated peptide/MHC complexes on their cell surfaces. In this way tumour-associated T-helper cell epitopes, alone or in combination with other tumour-associated peptides, can serve as active pharmaceutical ingredients of vaccine compositions which stimulate anti-tumour immune responses.

Since both types of response, CD8 and CD4 dependent, contribute jointly and synergistically to the anti-tumour effect, the identification and characterization of tumour-associated antigens recognised by either CD8+ CTLs (ligand: MHC class I molecule+peptide epitope) or by CD4-positive CTLs (ligand: MHC class II molecule+peptide epitope) is important in the development of tumour vaccines. It is therefore an object of the present invention, to provide novel amino acid sequences for peptides that are able to bind to MHC complexes of either class.

SUMMARY OF THE INVENTION

The present invention relates to peptides, nucleic acids and cells for use in immunotherapeutic methods. In particular, the present invention relates to the immunotherapy of cancer. The present invention furthermore relates to tumour-associated T-helper cell peptide epitopes, alone or in combination with other tumour-associated peptides that serve as active pharmaceutical ingredients of vaccine compositions which stimulate anti-tumour immune responses. The present invention relates to novel peptide sequences and their variants derived from HLA class I and class II molecules of human tumour cells which can be used in vaccine compositions for eliciting anti-tumour immune responses.

One embodiment of the invention provides peptides comprising a sequence that is selected from the group of SEQ ID NO: 1 to SEQ ID NO: 29 or a variant thereof which is 80% homologous to SEQ ID NO: 1 to SEQ ID NO: 29 or a variant, which will induce T cells cross-reacting with said peptide. In some embodiments, the peptides or variants have an overall length of between 8 and 100, preferably between 8 and 30, and most preferably between 8 and 16 amino acids. The peptides preferably have the ability to bind to a molecule of the human major histocompatibility complex (MHC) class-I or -II. The present invention also provides peptides that consist of or consist essentially of an amino acid sequence according to SEQ ID NO: 1 to SEQ ID NO: 29. The peptides may be modified, including modifications that include non-peptide bonds. The present invention also provides fusion proteins comprising the peptides, in particular comprising N-terminal amino acids of the HLA-DR antigen-associated invariant chain (Ii).

The present invention also provides nucleic acids encoding the peptides of the invention. The nucleic acid may be DNA, cDNA, PNA, CNA, RNA or combinations thereof. Another embodiment of the invention comprises expression vectors capable of expressing the nucleic acids of the invention. Host cells comprising nucleic acids or expression vectors of the present invention are also contemplated. The host cell may be an antigen presenting cell, in particular a dendritic cell.

Another embodiment also provides a peptide, nucleic acid, or expression vector of the present invention for use in medicine.

The present invention also provides methods for producing a peptide of the invention by culturing a host cell of the invention and isolating the peptide from the host cell or its culture medium.

The present invention also provides in vitro methods for producing activated cytotoxic T lymphocytes (CTL). The methods comprise contacting in vitro CTL with antigen loaded human class I or II MHC molecules expressed on the surface of a suitable antigen-presenting cell for a period of time sufficient to activate the CTL in an antigen specific manner. The antigen is a peptide of the present invention. The antigen may be loaded onto class I or II MHC molecules expressed on the surface of a suitable antigen-presenting cell by contacting a sufficient amount of the antigen with an antigen-presenting cell. The antigen-presenting cell may comprise an expression vector capable of expressing a peptide containing SEQ ID NO 1 to SEQ ID NO 29 or a variant thereof.

The present invention also provides activated cytotoxic T lymphocytes (CTL) produced by the methods described above, which selectively recognise a cell that aberrantly expresses a polypeptide comprising an amino acid sequence of the present invention.

Another embodiment of the present invention also provides methods of killing target cells in a patient in which target cells aberrantly express a polypeptide comprising an amino acid sequence of the present invention. The method comprises administering to the patient an effective number of cytotoxic T lymphocytes (CTL) as described above.

The present invention also provides use of any peptides, nucleic acids, expression vectors, or activated cytotoxic T lymphocytes according to the invention as a medicament or in the manufacture of a medicament. The medicament may be a vaccine and may be active against cancer. The cancer may be glioblastoma, colorectal, pancreatic, lung, renal or gastric cancer.

The present invention further provides a kit comprising peptides of the present invention.

Cells were primed and restimulated repeatedly with TGFBI-004 and then incubated with relevant TGFBI-004 (Well 1, 2, 3 and 4) and irrelevant (Neg. control) peptide, respectively. The analysis after IFNγ ELISPOT was performed on an ELISPOT Reader (CTL, Cleveland, USA). PHA-Ionomycin served as positive control. Numbers indicate the count of positive spots.

Figure 7A:
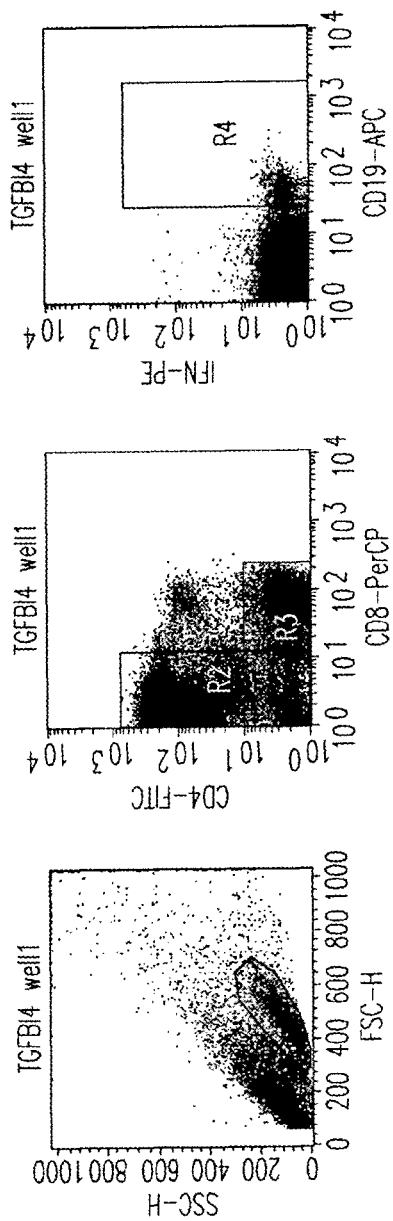
Figure 7B:
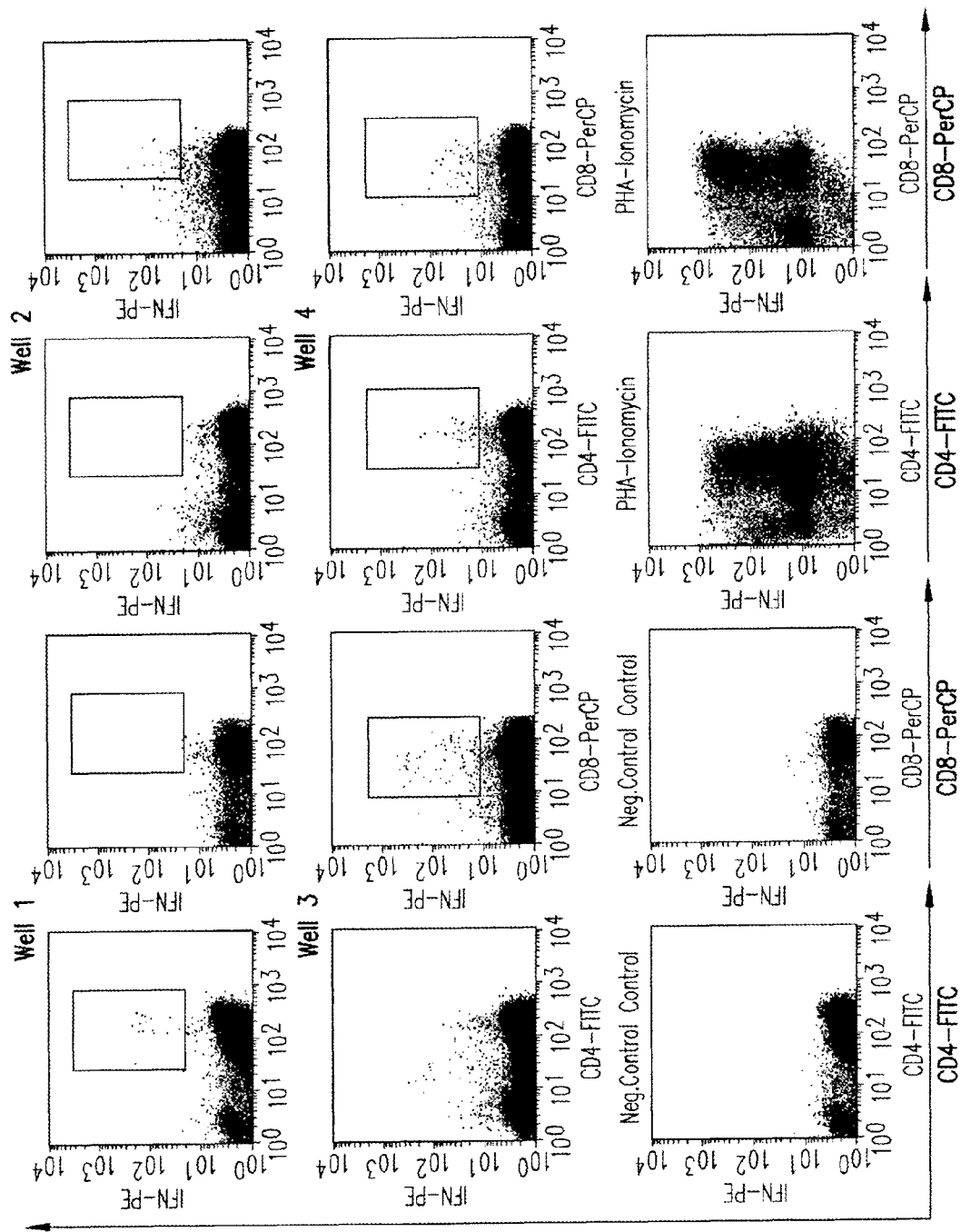

FIGS. 7a and 7b depict the in vitro immunogenicity of TGFBI-004 as detected by ICS after five stimulation cycles.

Cells were primed with TGFBI-004-loaded autologous DCs and restimulated repeatedly with autologous PBMCs plus TGFBI-004. For the read-out cells were incubated with relevant TGFBI-004 (Well 1, 2, 3 and 4) and irrelevant (Neg. Control) peptide, respectively. Additionally to the intracellular IFNγ staining, cells were also stained with CD4-FITC and OCD8-PerCP antibodies. The analysis was performed on a four-color FACSCalibur cytometer (BD Biosciences, Germany).

Figure 8A:
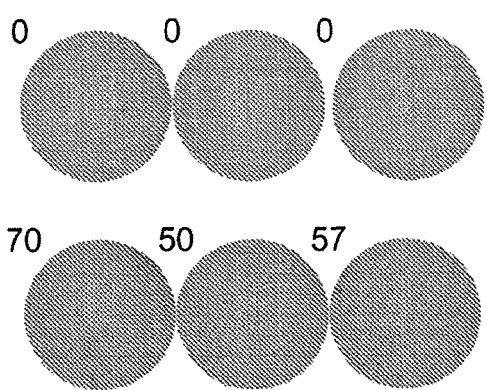
Figure 8B:
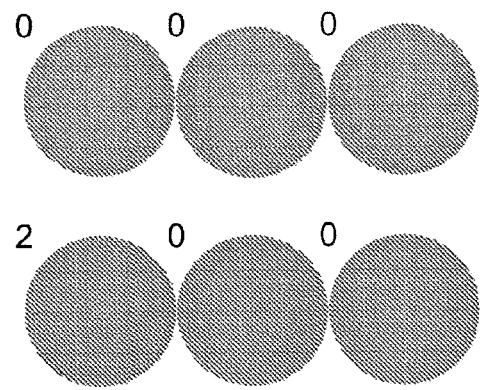

FIG. 8 depicts the ELISPOT analysis of IFNγ production by T-cell lines upon in vitro restimulation with the NOX-001 peptide. A. T-Cell line 7+ from donor HBC-154 (sorted CD8+ NOX-001 tetramer+); B. T-Cell line 7− from donor HBC-154 (sorted CD8+ NOX-001 tetramer-).

Sorted CD8+ NOX-001 tetramer+ (A.) and CD8+ NOX-001 tetramer− (B.) cells were analysed by IFNγ ELISPOT after restimulation with irrelevant (MLA-001) (upper wells) and relevant (NOX-001) (lower wells) peptide (10 μg/ml). Numbers indicate the count of positive spots.

Figure 9:
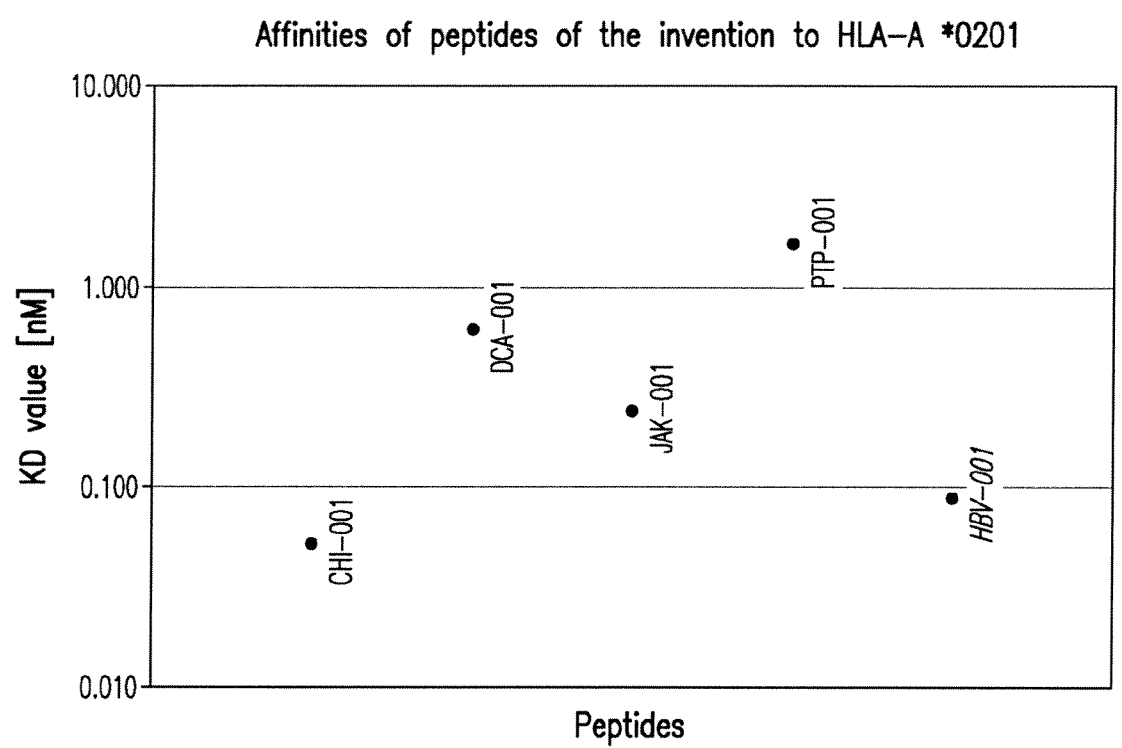

FIG. 9 shows the results of tests where affinities of peptides contained in the present invention to HLA-A*0201.

DETAILED DESCRIPTION OF THE INVENTION

In a first aspect the invention provides a peptide comprising a sequence that is selected from the group of SEQ ID NO: 1 to SEQ ID NO: 29 or a variant thereof which is 80% homologous to SEQ ID NO: 1 to SEQ ID NO: 29 or a variant, which will induce T-cells cross-reacting with said peptide.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX or analysis tools provided by public databases, may also be used.

A person skilled in the art will be able to assess whether T-cells induced by a variant of a specific peptide will be able to cross-react with the peptide itself by (Fong, L, et al., Proc. Natl. Acad. Sci. U.S.A, 98, 8809-8814); (Zaremba, S, et al., 2006, Eur. J. Immunol., 36, 1805-1814).

Table 1 shows the peptides, their respective SEQ ID NO: as well as information on the parent proteins.

TABLE 1

Peptides of the present invention

| SEQ ID NO: | Peptide Code | Sequence | HLA Alleles | Gene(s) |
|---|---|---|---|---|
| 1 | C20-001 | ALSNLEVTL | A*02 | C20orf42 |
| 2 | NOX-001 | ILAPVILYI | A*02 | NOX1 |
| 3 | PCN-001 | KLMDLDVEQL | A*02 | PCNA |
| 4 | PCN-002 | SMSADVPLV | A*02 | PCNA |
| 5 | TOP-001 | KIFDEILVNA | A*02 | TOP2A, TOP2B |
| 6 | TOP-002 | AAFVEELDKV | A*02 | TOP2B |
| 7 | CEA-009 | VLLLVHNLPQHLFG | class II | CEACAM5 |
| 8 | TGFBI-001 | ALFVRLLALA | A*02,A*02/B*13? | TGFBI |
| 9 | TGFBI-006 | GDKLEVSLKNNVVS | class II | TGFBI |
| 10 | TGFBI-007 | GKKLRVFVYRNSLCIENS | class II | TGFBI |
| 11 | TGFBI-008 | LKNNVVSVNKEPVAEPD | class II | TGFBI |
| | | KNNVVSVNKEPVAEPD | class II | TGFBI |
| | | KNNVVSVNKEPVA | class II | TGFBI |
| | | LKNNVVSVNKEPVA | class II | TGFBI |
| 12 | TGFBI-009 | NGVIHYIDELLIPDS | class II | TGFBI |
| | | GVIHYIDELLIPDSA | class II | TGFBI |
| 13 | TGFBI-010 | LNRILGDPEALRDL | class II | TGFBI |
| 14 | TGFBI-004 | TPPIDAHTRNLLRNH | class II | TGFBI |
| 15 | PTP-001 | ALTTLMHQL | A*02 | PTPRZ1 |
| 16 | GAL-001 | SLDPSSPQV | A*02 | GAL3ST1 |
| 17 | CHI-001 | SLWAGVVVL | A*02 | CHI3L2 |
| 18 | JAK-001 | KLTDIQIEL | A*02 | JAKMIP2 |
| 19 | AKR-001 | YLIHFPVSV | A*02 | AKR1C1, AKR1C2 |
| 20 | FN1-001 | IVDDITYNV | A*02 | FN1 |
| 21 | EGFR-002 | GAVRFSNNPALCNVES | class II | EGFR |
| | | AVRFSNNPALCNVES | class II | EGFR |
| | | AVRFSNNPALCNVE | class II | EGFR |
| 22 | EGFR-005 | NPTTYQMDVNPEGKYS | class II | EGFR |
| 23 | EGFR-006 | FKKIKVLGSGAFG | class II | EGFR |
| 24 | CHI3L1-001 | TTLIKEMKAEFIKEAQPG | class 11 | CHI3L1 |
| | | TLIKEMKAEFIKEAQPG | class II | CHI3L1 |
| | | TTLIKEMKAEFIKEA | class II | CHI3L1 |
| | | TLIKEMKAEFIKEA | class II | CHI3L1 |
| | | IKEMKAEFIKEAQPG | class II | CHI3L1 |
| | | TTLIKEMKAEFIKE | class II | CHI3L1 |
| 25 | CHI3L1-007 | VKSKVQYLKDRQLAG | class II | CHI3L1 |
| 26 | CHI3L1-008 | SRRTFIKSVPPFLRT | class II | CHI3L1 |
| 27 | DCA-001 | KLGDFGLATVV | A*02 | DCAMKL2 |
| 28 | KCN-001 | SLFDQVVKV | A*02 | KCNJ10 |
| 29 | GPM-001 | ALLSEVIQL | A*02 | GPM6B |

Chromosome 20 Open Reading Frame 42

C20orf42 is a focal adhesion protein involved in attachment of the actin cytoskeleton to the plasma membrane and in integrin-mediated cellular processes. Deficiency of C20orf42 as a result of loss-of-function mutations causes Kindler syndrome, an autosomal recessive genodermatosis characterized by skin blistering, progressive skin atrophy, photosensitivity and, occasionally, carcinogenesis (Herz, C, et al., 2006, J Biol. Chem., 281, 36082-36090). Recently, a severe gastrointestinal tract involvement with hemorrhagic colitis has been reported in a patient with a loss-of-function mutation (Sadler, E, et al., 2006, Arch. Dermatol., 142, 1619-1624).

In the context of cancer, C20orf42 has been described within studies investigating gene expression in cancer-relevant settings. It was found to be overexpressed in 70% of colon carcinomas and 60% of lung carcinomas tested (n=10). Normal tissue expression by Northern Blot was restricted to neuromuscular tissues (Weinstein, E J, et al., 2003, U, Biochim. Biophys. Acta, 1637, 207-216). Furthermore, C20orf42 has been identified as a gene involved in TGF-β-mediated cell migration and tumour invasion (Kloeker, S, et al., 2004, J. Biol. Chem., 279, 6824-6833).

NADPH Oxidase Homolog-1 (NOX1)

NOX1, is a growth factor-responsive enzyme that catalyzes formation of the reactive oxygen species superoxide ($O_2$—) and hydrogen peroxide ($H_2O_2$). Its expression was originally identified in colon, prostate, uterus, and proliferating vascular smooth muscle cells (Suh, Y. A. et al. 1999; Nature 401, 79-82). Its expression is linked to a number of biological responses including cellular proliferation, angiogenesis, and activation of cellular signalling pathways (Harper, R. W., et al., 2005, Arch. Biochem. Biophys. 435, 323-330).

NOX1 is highly expressed in the colon but its function in colonic physiology or pathology is still poorly understood. In normal tissues, NOX1 expression was low in the ileum, intermediate in the right colon, and high in the left colon. There was no statistical difference in NOX1 expression between samples derived from adenomas, well differentiated or poorly differentiated colon adenocarcinomas. NOX1 was highly expressed in colon epithelial cells, both within the crypts and on the luminal surface. In conclusion, NOX1 is an enzyme that is constitutively expressed in colon epithelium and is not directly associated with tumourigenesis (Szanto, I. et al. 2005, J. Pathol. 207, 164-176).

Immunohistochemistry showed that NOX1 was constitutively expressed in surface mucous cells. Adenomas and well differentiated adenocarcinomas up-regulated NOX1 expression. Nuclear factor (NF)-kappaB was predominantly activated in adenoma and adenocarcinoma cells expressing abundant NOX1, suggesting that NOX1 may stimulate NF-kappaB-dependent antiapoptotic pathways in colon tumours (Fukuyama, M. et al. 2005, Cancer Lett. 221, 97-104).

Wnt3a/beta-Catenin signalling has been described to induce NOX1 expression (Petropoulos, H., et al., 2002, J Biol. Chem. 277, 15393-15399).

Recently, reactive oxygen species have been suggested to induce endothelial apoptosis that subsequently induces the expression of various adhesion molecules for tumour cells. This indicates that by tackling the production of ROS preventing tumour recurrence at distant sites might be feasible (Ten, K M, et al., 2006, Br. J Cancer, 95, 1497-1503).

Proliferating Cell Nuclear Antigen (PCNA)

PCNA is found in the nucleus and is a cofactor of DNA polymerase delta. The encoded protein acts as a homotrimer and helps increase the processivity of leading strand synthesis during DNA replication. Therefore, it is expressed in all proliferating cells, especially tumour cells, and is used as a marker to detect proliferation.

DNA Topoisomerase II

TOP2A and TOP2B encode isoforms of a DNA topoisomerase, an enzyme that controls and alters the topologic states of DNA during transcription. This nuclear enzyme is involved in processes such as chromosome condensation, chromatid separation, and the relief of torsional stress that occurs during DNA transcription and replication. DNA topoisomerase catalyses the transient breaking and rejoining of two strands of duplex DNA which allows the strands to pass through one another, thus altering the topology of DNA. The two isoforms of this enzyme exist as likely products of a gene duplication event. The gene encoding the alpha form is localised to chromosome 17 and the beta gene is localised to chromosome 3.

TOP2A is the target for several anticancer agents and a variety of mutations in this gene have been associated with the development of drug resistance.

The TOP2A gene is located adjacent to the HER-2 oncogene, the most frequently amplified oncogene in breast cancer, at the chromosome location 17q12-q21 and is either amplified or deleted, with equal frequency, in almost 90% of HER-2 amplified primary breast tumours (Jarvinen, T A and Liu, E T; Topoisomerase II alpha gene (TOP2A) amplification and deletion in cancer-more common than anticipated, Cytopathology, 14, 309-313). Furthermore, TOP2A amplifications have been reported for other cancers.

Without TOP2A DNA replication and cell division are impossible. It has therefore become the main target of many antitumour therapy regimens, even though the exact mechanism of cell killing remains elusive (Kellner, U, et al., Lancet Oncol., 3, 235-243, 2002). The success of this approach is limited by the development of spontaneous resistance, and drug-induced DNA damage can increase malignancy. Recent data suggest that amplification and deletion of TOP2A may account for both sensitivity and resistance to TOP2A-inhibitor-chemotherapy, depending on the specific genetic defect at the TOP2A locus.

It is not clear whether the involvement of TOP2B in cancer is similar to TOP2A or whether there is a major difference between the two isoforms. TOP2B can at least supplement for some of the TOP2A activity (Sakaguchi, et al., J Cell Sci., 117, 1047-1054, 2004).

Carcinoembryonic Antigen-Related Cell Adhesion Molecule 5

Carcinoembryonic antigen (CEA=CEACAM5) is a 180 kDa heavily glycosylated membrane protein composed of three C21 g-like repeating units flanked by a N-terminal Ig V-like region and a C-terminal region, which includes glycophosphatidylinositol linkage region (Hegde, P, et al., Cancer Res., 61, 7792-7797, 2001).

As an oncofetal antigen, CEA is expressed during foetal development, but also, at low levels, in the gastrointestinal epithelium of adults. However, CEA is overexpressed in a high percentage of human tumours, including 90% of gastrointestinal, colorectal and pancreatic cancer, 70% of non-small cell lung cancer cells and 50% of breast cancers (Thompson, J A, et al., J Clin Lab Anal., 5, 344-366, 2005). Due to its high expression by tumour cells and its secretion to the serum, CEA has been broadly used as a tumour marker (Sikorska, H, et al., Cancer Detect. Prev., 12, 321-355, 1988) and is the standard serum marker for colorectal cancer monitoring (Locker, G Y, et al., J Clin Oncol, 24, 5313-5327, 2006).

Despite the overexpression of CEA in tumour cells, cancer patients do not normally show an immune response against this antigen (Orefice, S, et al., Tumouri, 68, 473-475, 1982) The immune system commonly becomes tolerant to CEA, because it is normally expressed at low levels in the body. However, in a series of clinical vaccine trials, the immunogenicity of CEA has been demonstrated (Sarobe, P, et al., Curr. Cancer Drug Targets., 4, 443-454, 2004), especially in colorectal carcinoma (CRC) (Mosolits, S, et al., Ann. Oncol., 16, 847-862, 2005), and CEA is the tumour associated antigen (TAA) with the greatest number of vaccine platforms tested in this tumour type (von Mehren, M; Oncol., 32, 76-84, 2005).

Several cytotoxic and helper T-cell epitopes have been described for CEA (Crosti, M, et al., J. Immunol., 176, 5093-5099, 2006; Novellino, L, et al., Cancer Immunol. Immunother., 54, 187-207, 2005; Ruiz, M, et al., Clin Cancer Res., 10, 2860-2867, 2004), enabling a variety of peptide-based vaccination trials in CRC (Babatz, J, et al, Cancer Immunol. Immunother., 55, 268-276, 2006; Fong, L, et al., Proc. Natl. Acad. Sci. U.S.A, 98, 8809-8814, 2001; Liu, K J, et al., Clin Cancer Res., 10, 2645-2651, 2004; Matsuda, K, et al., Cancer Immunol. Immunother., 53, 609-616, 2004; Ueda, Y, et al., Int. J. Oncol., 24, 909-917, 2004; Weihrauch, M R, et al., Clin Cancer Res., 11, 5993-6001, 2005). These and other clinical trials to date have demonstrated safety of CEA vaccinations and evidence for the induction of immune response against this antigen (von Mehren, M; Semin. Oncol., 32, 76-84, 2005).

Transforming Growth Factor, Beta-Induced (TGFBI)

TGFBI was first identified as a TGF-beta-inducible gene in a human lung adenocarcinoma cell line. It encodes for a secreted extracellular matrix protein, which is thought to act on cell attachment and extracellular matrix composition.

TGFBI was shown to be among the most significantly elevated genes in colorectal cancers and it is expressed at high levels in adenomas as well. Quantitative PCR results demonstrated strong elevation in both unpurified tumours and purified tumour epithelial cells. Accordingly, in situ hybridization experiments revealed TGFBI to be expressed in many cell types, in both the stromal and epithelial compartments (Buckhaults, P, et al., Cancer Res., 61, 6996-7001, 2001).

In a meta-analysis of studies investigating gene expression in colorectal carcinoma, TGFBI was identified as one of only nine genes described as upregulated repeatedly (4 studies for TGFBI) (Shih, W, et al., Oncol. Rep., 13, 517-524, 2005).

In human pancreatic tissues, there was a 32.4-fold increase in TGFBI mRNA levels in pancreatic cancers in comparison to normal control tissues. In situ hybridization analysis revealed that TGFBI mRNA was expressed mainly in the cancer cells within the pancreatic tumour mass (Schneider, D, et al., Biochim. Biophys. Acta, 1588, 1-6, 2002).

TGFBI was identified as a gene promoting angiogenesis in an in vitro model. Additionally, dramatically enhanced expression of TGFBI was detected in several tumours. Antisense oligonucleotides to TGFBI blocked both gene expression and endothelial tube formation in vitro, suggesting that TGFBI may play a critical role in endothelial cell-matrix interactions (Aitkenhead, M, et al., Microvasc. Res., 63, 159-171, 2002).

Protein Tyrosine Phosphatase, Receptor-Type, Zeta1 (PTPRZ1)

PTPRZ1 is a member of the receptor type protein tyrosine phosphatase family and encodes a single-pass type I membrane protein with two cytoplasmic tyrosine-protein phosphatase domains, an alpha-carbonic anhydrase domain and a fibronectin type-III domain. Expression of this gene is induced in gastric cancer cells (Wu, C W, et al., Cancer Lett., 242, 95-103, 2006), in the remyelinating oligodendrocytes of multiple sclerosis lesions (Harroch, S, et al., Nat. Genet., 32, 411-414, 2002), and in human embryonic kidney cells under hypoxic conditions (Wang, V, et al., Cancer Res., 65, 3299-3306, 2005).

Both the protein and transcript are overexpressed in glioblastoma cells, promoting their haptotactic migration (Lu, K V, et al., J Biol. Chem., 280, 26953-26964, 2005).

Furthermore, PTRPZ1 is frequently amplified at the genomic DNA level in glioblastoma (Mulholland, P J, et al., Cell Cycle, 5, 783-791, 2006).

Janus Kinase and Microtubule Interacting Protein 2 (JAKMIP2)

JAKMIP2 was identified as one of many known or putative downstream targets of PAX3-FKHR which were highly overexpressed in ARMS (Paediatric rhabdomyosarcoma, alveolar subtype) (Lae, M, et al., 2007, J. Pathol., 212, 143-151).

Fibronectin 1 (FN1)

Fibronectin is a high-molecular-weight glycoprotein containing about 5% carbohydrate that binds to receptor proteins that span the cell's membrane, called integrins. In addition to integrins, they also bind extracellular matrix components such as collagen, fibrin and heparin. There are several isoforms of fibronectin, all of which are the product of a single gene. FNs play a critical role in the maintenance of normal cell morphology, cell adhesion, migration, hemostasis, thrombosis, wound healing, differentiation and proliferation (Hynes, R O, Sci. Am., 254, 42-51, 1987).

The polymeric fibronectin, sFN, is formed in vitro by treating soluble fibronectin with a 76-aa peptide, III1-C (called Anastellin), which is derived from the first type III repeat in fibronectin. In vivo studies in tumour-bearing mice showed that systemic application of Anastellin or sFN suppressed tumour growth, angiogenesis and metastasis (Yi, M et al., Proc. Natl. Acad. Sci. U.S.A, 98, 620-624, 2001). Anginex is a synthetic 33-amino acid peptide that was originally modelled to reproduce the beta-sheet structure of antiangiogenic proteins. It has been shown that anginex initiates fibronectin polymerization and is inactive in mice that lack plasma fibronectin (Akerman, M E, et al., Proc. Natl. Acad. Sci. U.S.A, 102, 2040-2045). In a study, they examined the effects of FN on D-galactosamine (GalN)/lipopolysaccharide (LPS)-induced fulminant liver failure in mice. The results suggest that FN protected against GalN/LPS-induced liver failure by a mechanism involving inhibition of NF-kappaB activation, which caused down-regulation of TNF-alpha and involved up-regulation of IL-10, and elevation of Bcl-xL induced a blockage of apoptotic signals, by which apoptosis of hepatocytes caused by Ga1N/LPS was suppressed (Qiu, Z, et al., Shock, 25, 80-87, 2006). Other results indicate that FN stimulates human lung carcinoma cell proliferation and diminishes apoptosis in vitro by inducing COX-2 gene expression and PGE2 biosynthesis (Han, S., et al., Int. J. Cancer, 111, 322-331, 2004).

Fibronectin (FN) has been shown to undergo alternative splicing exclusively during organogenesis and tumourigenesis. One such splice variant, extradomain-B (ED-B) FN, is normally absent in normal adult tissues and is proposed to be a marker of tumoural angiogenesis (Khan, Z A, et al., Exp. Lung Res., 31, 701-711, 2005). Mhawech et al. showed that head and neck tumours with a positive staining for EDB had a trend to a significant lower overall survival of patients (Mhawech, P, et al., Oral Oncol., 41, 82-88, 2005).

Fibronectin expression regulates angiogenesis and vasculogenesis and participates in brain tissue responses to ischemia and seizures. The gene expression of fibronectin was significantly increased ($p<0.05$) in the SWS (Sturge-Weber syndrome) fibroblasts compared with that of fibroblasts from SWS normal skin (Comi, A M, et al., Pediatr. Res., 53, 762-7692, 2003). The fibronectin concentration was significantly higher in ovarian cancers compared with benign ovarian tumours and normal ovaries. Fibronectin concentration significantly elevated in ovarian cancer patients with recurrent disease compared with ovarian cancer patients without recurrence. The expression of tumour-derived matriolytic enzymes and fibronectin are important in the growth of ovarian tumours (Demeter, A, et al., Orv. Hetil., 145, 1617-1624, 2004). The fact that FN was one of the only two genes significantly down-regulated out of the 1,176 genes analyzed in a study stresses the hypothesis that FN may behave as an important metastasis suppressor gene in mammary cancer (Urtreger, A J, et al., Oncol. Rep., 16, 1403-1410).

In a report, they found that three soluble fibronectin peptides (RGD, CS-1, and FN-C/H-V) induce apoptosis in lung fibroblasts. Apoptosis occurred by disruption of adhesion (anoikis). The use of small fibronectin peptides to promote fibroblast apoptosis warrants further study as possible antifibrotic therapy (Hadden, H L et al., Am. J. Respir. Crit. Care Med, 162, 1553-1560, 2000). Another study has demonstrated that fibronectin (FN) stimulates human non-small cell lung carcinoma (NSCLC) cell proliferation. They show that FN increases MMP-9 protein, mRNA expression, and gelatinolytic activity in NSCLC cells (Han, S, et al., J Biol. Chem., 281, 29614-29624, 2006). In one study, they investigated whether the tumour-suppressive effects of vitamin D (VD) compounds may also be mediated by mechanisms that govern cell adhesiveness. Introduction of small interfering RNA against FN resulted in down-regulation of FN expression and diminished cell adhesiveness to a collagen-type I matrix. Their findings highlight the significance of FN in modulating thyroid cancer cell adhesiveness and, at least in part, in mediating VD actions on neoplastic cell growth (Liu, W, et al. Mol. Endocrinol., 19, 2349-2357, 2005).

The generation of tumour-associated FN isoforms allows the development of specific ligands (e.g., antibodies), which can be used for the selective delivery of therapeutic agents to the tumour environment. FN is being used as a target for biomolecular intervention, both for the development of inhibitory molecules that block the interaction of FN with integrins and other receptors on the cell surface, and for the development of ligand-based targeted imaging and therapeutic strategies (Kaspar, M, et al., Int. J. Cancer, 118, 1331-1339, 2005). One study demonstrated that the treatment by in vivo expression of a recombinant CBD-HepII polypeptide of FN, designated as CHSO, strongly inhibited the tumour growth, tumour invasion and angiogenesis. The gene therapy with CHSO not only prolonged the survival of mice bearing hepatocarcinoma in the liver, but also suppressed the growth and invasive ability of tumour in spleen and its metastasis to liver. Taken together, these findings suggest a prospective utility of CHSO in the gene therapy of liver cancer (Liu, Y, et al., Int. J. Cancer, 2007, 121(1):184-92). Fibronectin (FN) has a cryptic functional site (YTIYVIAL sequence within the 14th type III repeat) opposing cell adhesion to extracellular matrix. A 22-mer FN peptide containing this site, termed FNIII14, inhibits beta1 integrin-mediated adhesion without binding to integrins. The study shows that FNIII14 has the potential to prevent lymphoma cell metastasis (Kato, R, et al., Clin Cancer Res., 8, 2455-2462, 2002).

Epidermal Growth Factor Receptor (EGFR)

EGFR plays an important role in the regulation of normal cell proliferation, differentiation and survival. For this reason EGFR status is often altered in a range of human tumour types and generally correlates with a poor prognosis. In neoplastic cells it contributes to their growth and survival through various divergent pathways (Maehama, T, et al., J Biol. Chem., 273, 13375-13378, 1998). EGFR abnormalities are one of the most common molecular aberrations in glioblastoma (Zawrocki, A et al., Folia Neuropathol., 43, 123-132, 2005).

The EGFR amplification and mRNA overexpression are frequent in high grade gliomas of astrocytic origin, and are always strongly associated with an increased level of the EGFR protein (Wong, A J, et al., 1987, Proc. Natl. Acad. Sci. U.S.A, 84, 6899-6903; Chaffanet, M, et al., 1992, Eur. J. Cancer, 28, 11-17). Protein overexpression without gene amplification has been reported in up to 27% of GBMs, but less malignant astrocytomas and oligodendrogliomas were also reported to demonstrate the EGFR overexpression without the underlying gene amplification (Reifenberger, J, et al., 1996, Am. J. Pathol., 149, 29-35).

The prognostic implications of the EGFR amplification/overexpression in brain tumours are controversial. Some authors did not find any influence of the EGFR amplification/overexpression on survival of the patients (Olson, J J, et al., 1998, Clin Cancer Res., 4, 215-222; Newcomb, E W, et al., 1998, Brain Pathol., 8, 655-667; Waha, A, et al., 1996, J Neurosurg., 85, 634-641) while the others concluded that these alterations were a negative prognostic factor (Etienne, M C, et al., 1998, Clin Cancer Res., 4, 2383-2390; Jaros, E, et al., 1992, Br. J. Cancer, 66, 373-385; Schlegel, J, et al., 1994, Int. J. Cancer, 56, 72-77; Zhu, A, et al., 1996, Int. J. Radiat. Oncol. Biol Phys., 34, 809-815).

There exist a few treatment approaches to the EGFR molecule on the cancer cell. The most extensively studied include: specific antibody therapy by means of unarmed antibodies or antibodies conjugated with toxins, liposomes or nuclides, and the use of inhibitors of the receptor tyrosine kinase. There are several types of monoclonal antibodies directed against the EGFRwt. Their use results in blocking access to the receptor for its ligands (cetuximab) and/or rapid internalization of the receptor (ABX-EGF) (Sridhar, S S, et al., 2003, Lancet Oncol., 4, 397-406). As the EGFRwt occurs also on the surface of normal cells, side effects may limit its use.

EGFR is overexpressed in head and neck squamous cell carcinoma (HNSCC) where expression levels correlate with decreased survival. Therapies that block EGFR have shown limited efficacy in clinical trials and primarily when combined with standard therapy. EGFRvIII is expressed in HNSCC where it contributes to enhanced growth and resistance to targeting wild-type EGFR. The antitumour efficacy of EGFR targeting strategies may be enhanced by the addition of EGFRvIII-specific blockade (Sok, J C, et al., 2006, Clin Cancer Res., 12, 5064-5073).

Another strategy is to selectively induce the death of glioblastoma cells and other cancer cells that over-express the EGF receptor. Using a non-viral delivery vector that homes to the EGF receptor, synthetic anti-proliferative dsRNA (polyinosine-cytosine [poly IC]), a strong activator of apoptosis, was targeted selectively to cancer cells. EGFR-targeted poly IC induced rapid apoptosis in the target cells in vitro and in vivo. Tumoural delivery of the EGFR-targeted poly IC induced the complete regression of pre-established intracranial tumours in nude mice, with no obvious adverse toxic effects on normal brain tissue. A year after treatment completion the treated mice remain cancer-free and healthy (Shir, A, et al., 2006, PLoS. Med, 3, e6-).

The application of small interfering RNAs (siRNAs) has become an effective and highly specific tool to modulate gene expression, and a wide range of oncogenes have been silenced successfully. siRNA-mediated down-regulation of EGFR was shown in two established glioma cell lines with different EGFR expression levels (U373 MG, LN18). The expression of EGFR mRNA and protein was down-regulated by 70-90%. However, siRNA treatment had no inhibitory effect on cell proliferation, migration and activation status of EGFR-coupled signalling cascades. In accordance with these results, gene expression analysis with microarrays revealed only small, albeit specific changes in expression patterns. In conclusion, these data indicate that the specific down-regulation of EGFR might not be sufficient for a single agent therapeutic approach in malignant glioma (Vollmann, A, et al., 2006, Int. J. Oncol., 28, 1531-1542).

Several clinical studies exist have been conducted that show promising results. For example, h-R3 is a humanized monoclonal antibody that recognize the EGFR external domain with high affinity, inhibiting tyrosine kinase activation. To evaluate safety, immunogenicity and preliminary efficacy of h-R3 in newly diagnosed high-grade glioma patients, a Phase I/II trial was conducted (Ramos, T C, et al., 2006, Cancer Biol Ther., 5, 375-379).

EKB-569 is a potent, low molecular weight, selective, and irreversible inhibitor of epidermal growth factor receptor (EGFR) that is being developed as an anticancer agent. A phase 1, dose-escalation study was conducted in Japanese patients. Based on RECIST criteria, they had stable disease but radiographic tumour regression was observed (Yoshimura, N, et al., 2006, Lung Cancer, 51, 363-368).

Gefitinib, a specific inhibitor of epidermal growth factor receptor (EGFR)-associated tyrosine kinase has demonstrated efficacy in a subgroup of patients with non-small-cell lung carcinoma (NSCLC) who fail conventional chemotherapy. It is also reported to have an antitumour effect in brain metastases from NSCLC. Additionally, EGFR mutations have shown a strong association with gefitinib sensitivity for NSCLC. The efficacy of gefitinib in brain metastases from NSCLC was assessed and the association of this efficacy with EGFR mutations evaluated. Gefitinib appears to be effective in treating brain metastases in a subgroup of patients. The data suggested a possible association between the efficacy of gefitinib in the treatment of brain metastases and EGFR mutations (Shimato, S, et al., 2006, Neuro.-oncol., 8, 137-144).

Chitinase 3-Like 2 (CHI3L2)

CHI3L2 was originally identified from chondrocytes. It has been frequently described as a target antigen in rheumatoid arthritis. No relevant association of CHI3L2 with cancer was identified. Chitinase 3-like proteins have been implied in stimulating proliferation of human connective tissue cells, e.g. fibroblasts, by activating extracellular signal-regulated kinase and PKB mediated signalling pathways (Recklies A D, et al., Biochem J. 2002; 365:119-126). In mice chitinase 3-like proteins have been found to be strongly upregulated in *Helicobacter*-induced gastric cancer models (Takaishi S, et al. Cancer Sci. 2007 (3): 284-293)

Doublecortin and CaM Kinase-Like 2 (DCAMKL2)

The microtubule (MT)-associated DCX protein plays an essential role in the development of the mammalian cerebral cortex. Identification of a protein kinase, doublecortin kinase-2 (DCAMKL2), with a domain (DC) highly homologous to DCX was reported. DCAMKL2 has MT binding activity associated with its DC domain and protein kinase activity mediated by a kinase domain, organized in a structure in which the two domains are functionally independent.

Overexpression of DCAMKL2 stabilizes the MT cytoskeleton against cold-induced depolymerization. Autophosphorylation of DCAMKL2 strongly reduces its affinity for MTs. DCAMKL2 and DCX mRNAs are nervous system-specific and are expressed during the period of cerebrocortical lamination. DCX is down-regulated postnatally, whereas DCAMKL2 persists in abundance into adulthood, suggesting that the DC sequence has previously unrecognized functions in the mature nervous system. In sympathetic neurons, DCAMKL2 is localized to the cell body and to the terminal segments of axons and dendrites.

DCAMKL2 may represent a phosphorylation-dependent switch for the reversible control of MT dynamics in the vicinity of neuronal growth cones. The patterns of expression, functional activities, regulation, and localization of DCAMKL2 suggest that it functions in parallel to, or in concert with, other members of the DC gene family (DC domain-encoding genes) in events important for neural development and, potentially, in those characteristic of mature nervous systems. DCAMKL2 is composed of two functional and independent domains, an MT-binding and -stabilizing domain (the DC sequence) and a kinase domain with protein phosphotransferase activity.

It was suggested that the DC sequence plays a critical role in transducing extracellular cues and their intracellular signals into changes in MT dynamics. In particular, based on an ability to interact with MTs in a fashion regulated by phosphorylation and to localize to terminal segments of axons and dendrites, regions in which MTs are dynamically unstable, DCAMKL2 should be considered a potential candidate mediator of the rapid cytoskeletal rearrangements that occur in response to neuronal signalling events (Edelman, A M, et al., 2005, J Biol. Chem., 280, 8531-8543).

ATP-Sensitive Inward Rectifier Potassium Channel 10 (KCNJ10)

The major function of inwardly rectifying potassium channels (Kir) is in establishing the high potassium (K+) selectivity of the glial cell membrane and strongly negative resting membrane potential (RMP), which are characteristic physiological properties of glia. The classical property of Kir is that K+ flows inwards when the RMP is negative to the equilibrium potential for K+(E(K)), but at more positive potentials outward currents are inhibited. A feature of CNS glia is their specific expression of the KCNJ10 subtype, which is a major K+ conductance in glial cell membranes and has a key role in setting the glial RMP. Hence, Kir, and in particular KCNJ10 are key regulators of glial functions, which in turn determine neuronal excitability and axonal conduction (Butt, A M et al., 2006, J Cell Mol. Med, 10, 33-44).

Diminished potassium and glutamate buffering capabilities of astrocytes result in hyperexcitability of neurons and abnormal synaptic transmission. KCNJ10 channels are primarily responsible for significant hyperpolarization of cortical astrocytes and are likely to play a major role in potassium buffering. Significant inhibition of glutamate clearance in astrocytes with knock-down of KCNJ10 highlights the role of membrane hyperpolarization in this process (Kucheryavykh, Y V, et al., 2006, Glia, Volume 55 Issue 3, Pages 274-281).

KCNJ10 spatial buffering of extracellular K(+) in the central nervous system can only be performed due to the non-uniform distribution of KCNJ10 across the surface of the glial cell. A mislocalization of KCNJ10 in various human brain tumours (low- and high-grade astrocytomas and oligodendrogliomas) was observed, suggesting that buffering capacity of glial cells may be compromised, leading to water influx (cytotoxic edema) (Warth, A, et al., 2005, Acta Neuropathol. (Berl), 109, 418-426). KCNJ10 was also upregulated in astrocytes in damaged brain. The following hypothesis was proposed: in astrocytes, under normal conditions, AQP4 couples water transport with KCNJ10 mediated K+ siphoning, but in pathological states, AQP4 facilitates the flow of brain oedema fluid, and KCNJ10 buffers increased extracellular K+ (Saadoun, S, et al., 2003, J Clin Pathol., 56, 972-975).

In addition to the peptides shown in SEQ ID NO:1-29, as discussed above, the present invention further includes variants of these peptides a slong as they will induce T-cells cross reacting with the peptide. By a "variant" of the given amino acid sequence the inventors mean that the side chains of, for example, one or two of the amino acid residues are altered (for example by replacing them with the side chain of another naturally occurring amino acid residue or some other side chain) so that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A or -DR, and so that it at least maintains, if not improves, the ability to generate activated CTL that can recognise and kill cells that express a polypeptide containing an amino acid sequence as defined in the aspects of the invention. As can derived from the database, certain positions of HLA-A binding peptides are typically anchor residues forming a core sequence fitting to the binding motif of the HLA binding groove.

Those amino acid residues that are not essential to interact with the T-cell receptor can be modified by replacement with another amino acid whose incorporation does not substantially effect T-cell reactivity and does not eliminate binding to the relevant MHC. Thus, apart from the proviso given, the peptide of the invention may be any peptide (by which term the inventors include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions that do not interfere with the function of the core sequence (i.e. are deemed as irrelevant for the interaction of the peptide and all or a subset of T-cell clones recognising the natural counterpart). The N- and/or C-terminal extensions can, for example, be between 1 to 10 amino acids in length, respectively. These peptides can be used either directly to load MHC class II molecules or the sequence can be cloned into the vectors according to the description herein below. As these peptides constitute the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1000 residues, preferably fewer than 500 residues, more preferably fewer than 100 residues. Accordingly the present invention also provides peptides and variants thereof wherein the peptide or variant has an overall length of between 8 and 100, preferably between 8 and 30, and most preferred between 8 and 16, namely 8, 9, 10, 11, 12, 13, 14, 15, or 16 amino acids.

Correspondingly, naturally occurring or artificial variants that induce T-cells cross-reacting with a peptide of the invention are often length variants. Examples for such naturally occurring length variants are given in Table 1 for SEQ ID NOs: 11 and 12, and 21 and 24, respectively.

If a peptide longer than around 12 amino acid residues is used directly to bind to a MHC class II molecule, it is preferred that the residues that flank the core HLA binding region do not substantially affect the ability of the peptide to bind specifically to the binding groove of the MHC class II molecule or to present the peptide to the CTL. However, as already indicated above, it will be appreciated that larger peptides may be used, e.g. when encoded by a polynucleotide, since these larger peptides may be fragmented by suitable antigen-presenting cells.

It is also possible, that MHC class I epitopes, although usually between 8-10 amino acids long, are generated by peptide processing from longer peptides or proteins that include the actual epitope. Similar to MHC class II epitopes, it is preferred that the residues that flank the binding region do not substantially affect the ability of the peptide to bind specifically to the binding groove of the MHC class 1 molecule or to present the peptide to the CTL nor mask the sites for proteolytic cleavage necessary to expose the actual epitope during processing.

Accordingly, the present invention also provides peptides and variants of MHC class I epitopes having an overall length of between 8 and 100, preferably between 8 and 30, and most preferred between 8 and 16, namely 8, 9, 10, 11, 12, 13, 14, 15, or 16 amino acids.

Of course, the peptide or variant according to the present invention will have the ability to bind to a molecule of the human major histocompatibility complex (MHC) class I or II. Binding of a peptide or a variant to a MHC complex may be tested by methods known in the art, for example those described in example 4 of the present invention or those described in the literature for different MHC class II alleles (e.g. Vogt A B, et al., J. Immunol. 1994; 153(4):1665-1673; Malcherek G, et al., J. Immunol. 1994; 153(3):1141-1149; Manici S, et al., J Exp Med. 1999; 189(5): 871-876; Hammer J, et al., J Exp Med. 1995 181(5):1847-1855; Tompkins S M, et al., J Immunol Methods. 1993; 163(2): 209-216; Boyton R J, et al., Int Immunol. 1998 (12):1765-1776).

In a particularly preferred embodiment of the invention, the peptide consists or consists essentially of an amino acid sequence according to SEQ ID NO: 1 to SEQ ID NO: 29.

"Consisting essentially of" shall mean that a peptide according to the present invention, in addition to the sequence according to any of SEQ ID NO: 1 to SEQ ID NO: 29 or a variant thereof, contains additional N- and/or C-terminally located stretches of amino acids that are not necessarily forming part of the peptide that functions as an epitope for MHC molecules epitope.

Nevertheless, these stretches can be important to provide an efficient introduction of the peptide into the cells. In one embodiment of the present invention, the peptide of the present invention is a fusion protein which comprises, for example, the 80 N-terminal amino acids of the HLA-DR antigen-associated invariant chain (p33, in the following "Ii") as derived from the NCBI, GenBank Accession-number X00497 (Strubin, M., at al., EMBO J. 3 (4), 869-872 (1984)).

In addition the peptide or variant may be modified further to improve stability and/or binding to MHC molecules to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC and T helper cell responses, these pseudopeptides are useful. Retro-inverse peptides containing NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains that involves polypeptides synthesised by standard procedures and the non-peptide bond synthesised by reacting an amino aldehyde and an amino acid in the presence of NaCNBH$_3$.

Peptides comprising the sequences described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxyl termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples of these modifications are well known in the art and are summarised in for example, R. Lundblad, Chemical Reagents for Protein Modification, 3rd ed. CRC Press, 2005, which is incorporated herein by reference. Chemical modification of amino acids includes, but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY, 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of Pierce Chemical Company and Sigma-Aldrich and others provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycation of proteins. Methionine residues in proteins can be modified with e.g. iodoacetamide, bromoethylamine, chloramine T. Tetranitromethane and N-acetylimidazole can be used for the modification of tyrosyl residues. Cross-linking via the formation of dityrosine can be accomplished with hydrogen peroxide/copper ions. Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Generally, peptides and variants (at least those containing peptide linkages between amino acid residues) may be synthesised by the Fmoc-polyamide mode of solid-phase peptide synthesis as disclosed by Lu et al (1981) J. Org. Chem. 46, 3433 and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethandithiol, phenol, anisole and water, the exact choice depending on the constituent amino acids of the peptide being synthesized. In addition, a combination of solid phase and solution phase methodologies for the synthesis of peptides is possible (see, for example, Bruckdorfer T, et al., Curr Pharm Biotechnol. 2004 February; 5(1):29-43 and the references as cited therein). Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (UK) Ltd, Nottingham NG7 2QJ, UK.

Purification may be effected by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide or peptide variant of the invention. The polynucleotide may be e.g. DNA, cDNA, PNA, CNA, RNA, mRNA, and siRNA or combinations thereof, either single- and/or double-stranded, or native or stabilised forms of polynucleotides, such as e.g. polynucleotides with a phosphorothiate backbone, and it may or may not contain introns so long as it codes for the peptide. Of course, only peptides containing naturally occurring amino acid residues joined by naturally occurring peptide bonds are encodable by a polynucleotide. A still further aspect of the invention provides an expression vector capable of expressing a polypeptide according to the invention.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc, New Haven, Conn., USA.

A desirable method of modifying DNA encoding the polypeptide of the invention utilizes the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art.

If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued Apr. 3, 1984 to Rutter et al., 4,530,901 issued Jul. 23, 1985 to Weissman, 4,582,800 issued Apr. 15, 1986 to Crowl, 4,677,063 issued Jun. 30, 1987 to Mark et al., 4,678,751 issued Jul. 7, 1987 to Goeddel, 4,704,362 issued Nov. 3, 1987 to Itakura et al., 4,710,463 issued Dec. 1, 1987 to Murray, 4,757,006 issued Jul. 12, 1988 to Toole, Jr. et al., 4,766,075 issued Aug. 23, 1988 to Goeddel et al. and 4,810,648 issued Mar. 7, 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells. Preferably, the system can be mammalian cells such as colorectal cancer- or glioblastoma cells such as those available from the ATCC Cell Biology Collection.

A typical mammalian cell vector plasmid is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells, which are human embryonic kidney cells. Preferred insect cells are Sf9 cells, which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al. (1972) Proc. Natl. Acad. Sci. USA 69, 2110 and Sambrook et al. (1989) Molecular Cloning, A Laboratory Manual, Cold Spring Harbor Laboratory, Cold Spring Harbor, N.Y. Transformation of yeast cells is described in Sherman et al. (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may be used to express the peptides of the invention so that they may be loaded into appropriate MHC molecules. Thus, the present invention provides a host cell comprising a nucleic acid or an expression vector according to the invention.

In a preferred embodiment the host cell is an antigen presenting cell (APC), in particular a dendritic cell or antigen presenting cell. APCs loaded with a recombinant fusion protein containing prostatic acid phosphatase (PAP) are currently under investigation for the treatment of prostate cancer (Sipuleucel-T) (Small E J, et al., J Clin Oncol. 2006; 24(19): 3089-3094; Rini B I, et al., Cancer. 2006; 107(1):67-74).

A further aspect of the invention provides a method of producing a peptide or its variant. The method comprises culturing the host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred routes of peptide injection are s.c., i.d., i.p., i.m., and i.v. Preferred routes of DNA injection are i.d., i.m., s.c., i.p. and i.v. Doses of between 50 μg and 1.5 mg, preferably 125 μg to 500 μg, of peptide or DNA may be given and will depend from the respective peptide or DNA. Doses of this range were successfully used in previous trials (Brunsvig P F, et al., 2006; 55(12):1553-1564; M. Staehler, et al., ASCO meeting 2007; Abstract No 3017).

An important aspect of the present invention is an in vitro method for producing activated CTL. The method comprises contacting in vitro CTL with antigen loaded human class I or II MHC molecules expressed on the surface of a suitable antigen-presenting cell for a period of time sufficient to activate the CTL in an antigen specific manner. The antigen is a peptide according to the invention. Preferably a sufficient amount of the antigen is used with an antigen-presenting cell.

In case of a MHC class II epitope used as an antigen, the CTL are CD4-positive helper cells, preferably of $T_{H1}$-type. The MHC class II molecules may be expressed on the surface of any suitable cell and preferred the cell does not naturally express MHC class II molecules (in which case the cell is transfected to express such a molecule). Alternatively, if the cell naturally expresses MHC class II molecules, the cell is defective in the antigen-processing or antigen-presenting pathways. In this way, it is possible for the cell expressing the MHC class II molecule to be primed substantially completely with a chosen peptide antigen before activating the CTL.

The antigen-presenting cell (or stimulator cell) typically has MHC class II molecules on its surface and preferably is itself substantially incapable of loading said MHC class II molecule with the selected antigen. The MHC class II molecule may readily be loaded with the selected antigen in vitro.

Preferably the mammalian cell lacks or has a reduced level or has reduced function of the TAP peptide transporter. Suitable cells which lack the TAP peptide transporter include T2, RMA-S and *Drosophila* cells. TAP is the Transporter associated with Antigen Processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre and Ljunggren (1985) J. Exp. Med. 162,1745.

It is preferable that the host cell does not express MHC class 1 molecules before transfection. Preferably the stimulator cell expresses a molecule important for T-cell costimulation such as any of B7.1, B7.2, ICAM-1 and LFA 3.

The nucleic acid sequences of numerous MHC class II molecules, and of the costimulator molecules, are publicly available from the GenBank and EMBL databases.

Similarly, in the case of a MHC class I epitope used as an antigen, the CTL are CD8-positive helper cells. The MHC class 1 molecules may be expressed on the surface of any suitable cell and it is preferred that cell does not naturally express MHC class 1 molecules (in which case the cell is transfected to express such a molecule). Alternative, if the cell naturally expresses MHC class 1 molecules, it is defective in the antigen-processing or antigen-presenting pathways. In this way, it is possible for the cell expressing the MHC class 1 molecule to be primed substantially completely with a chosen peptide antigen before activating the CTL.

If an antigen-presenting cell is transfected to express such an epitope, preferably the cell comprises an expression vector capable of expressing a peptide containing SEQ ID NO: 1 to SEQ ID NO: 29 or its variant amino acid sequence.

A number of other methods may be used for generating CTL in vitro. For example, the methods described in Peoples et al (1995) Proc. Natl. Acad. Sci. USA 92, 432-436 and Kawakami et al (1992) J. Immunol. 148, 638-643 use autologous tumour-infiltrating lymphocytes in the generation of CTL. Plebanski et al (1995) Eur. J. Immunol. 25, 1783-1787 makes use of autologous peripheral blood lymphocytes (PLBs) in the preparation of CTL. Jochmus et al (1997) J. Gen. Virol. 78, 1689-1695 describes the production of autologous CTL by employing pulsing dendritic cells with peptide or polypeptide, or via infection with recombinant virus. Hill et al (1995) J. Exp. Med. 181, 2221-2228 and Jerome et al (1993) J. Immunol. 151, 1654-1662 make use of B cells in the production of autologous CTL. In addition, macrophages pulsed with peptide or polypeptide, or infected with recombinant virus, may be used in the preparation of autologous CTL. S. Walter et al., J. Immunol. 2003 Nov. 15; 171(10): 4974-8 describe the in vitro priming of T-cells by using artificial antigen presenting cells, which is also a suitable method for generating T-cells against the peptide of choice.

Allogeneic cells may also be used in the preparation of CTL and an exemplary method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition, plant viruses may be used (see, for example, Porta et al (1994) Virology 202, 449-955, which describes the development of cowpea mosaic virus as a high-yielding system for the presentation of foreign peptides.

The activated CTL that are directed against the peptides of the invention are useful in therapy. Thus, a further aspect of the invention provides activated CTL obtainable by the foregoing methods of the invention.

Activated CTLs, produced by the above method will selectively recognise a cell that aberrantly expresses a polypeptide comprising an amino acid sequence of SEQ ID NO: 1 to 29.

Preferably, the CTL recognises the cell by interacting through its TCR with the HLA/peptide-complex (for example, binding). CTLs are useful in a method of killing target cells in a patient wherein the target cells aberrantly express a polypeptide comprising an amino acid sequence of the invention. The patient is administered an effective number of the activated CTLs. The CTLs administered to the patient may be derived from the patient and activated as described above (i.e. they are autologous CTLs). Alternatively, the CTLs are not from the patient but are from another individual. Of course, preferably the donor a healthy individual. By "healthy individual" it is meant that the individual is generally in good health, preferably has a competent immune system and, more preferably, is not suffering from any disease that can be readily tested and detected.

The target cells in vivo for the CD4-positive CTL according to the present invention can be cells of the tumour (which sometimes express MHC class II) and/or stromal cells surrounding the tumour (tumour cells) (which sometimes also express MHC class II; (Dengjel, J, et al., 2006, Clin Cancer Res., 12, 4163-4170)).

The CTLs of the invention may be used as active ingredients in a therapeutic composition. Thus, the invention also provides a method of killing target cells in a patient where the target cells aberrantly express a polypeptide comprising an amino acid sequence of the invention. The method comprises administering to the patient an effective number of CTLs as defined above.

By "aberrantly expressed" we include the meaning that the polypeptide is over-expressed compared to normal levels of expression or that the gene is silent in the tissue from which the tumour is derived but in the tumour it is expressed. By "over-expressed" we mean that the polypeptide is present at a level at least 1.2× that present in normal tissue; preferably at least 2× and more preferably at least 5× or 10× the level present in normal tissue.

CTLs may be obtained by methods known in the art, e.g. those described above.

Protocols for this so-called adoptive transfer of CTL are well known in the art and can be found, e.g. in (Rosenberg, S A, et al., 1987, N. Engl. J. Med., 316, 889-897; Rosenberg, S A, et al., 1988, N. Engl. J. Med, 319, 1676-1680; Dudley, M E, et al., 2002, Science, 298, 850-854; Yee, C, et al., 2002, Proc. Natl. Acad. Sci. U.S.A, 99, 16168-16173; Dudley, M E, et al., M M, 2005, J. Clin. Oncol., 23, 2346-2357); reviewed in Nat. Rev. Immunol., 6, 383-393) and (Morgan, R A, et al., 2006, Science) 314 (5796):126-129).

Any molecule of the invention, i.e. the peptide, nucleic acid, expression vector, cell, activated CTL, T-cell receptor or the nucleic acid encoding it is useful for the treatment of disorders, characterised by cells escaping an immune response. Therefore, any molecule of the present invention may be used as medicament or in the manufacture of a medicament. The molecule may be used by itself or combined with other molecule(s) of the invention or (a) known molecule(s).

Preferably the medicament is a vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2 The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides of the present invention are expected to stimulate CD4 or CD8 CTL. However, stimulation is more efficient in the presence of help provided by T-cells positive for the opposite CD. Thus, for MHC Class II epitopes that stimulate CD4 CTLm the fusion partner or sections of a hybrid molecule suitably provide epitopes that stimulate CD8-positive T-cells. On the other hand, for MHC Class I epitopes that stimulate CD8 CTLm the fusion partner or sections of a hybrid molecule suitably provide epitopes that stimulate CD4-positive T-cells. CD4- and CD8-stimulating epitopes are well known in the art and include those identified in the present invention.

In one aspect of the invention, the vaccine comprises at least one peptide, preferably two to 50, more preferably two to 25, even more preferably two to 15 and most preferably two, three, four, five, six, seven, eight, nine, ten, eleven, twelve or thirteen peptides of the invention or additional peptides. The peptide(s) may be derived from one or more specific TAAs and may bind to MHC class I and/or class II molecules.

Preferably when the peptides of the invention are used in a vaccine or medicament of the invention, they are present as a salt, such as for example, but not limited to an acetate salt or a chloride salt. Example 7 provides studies of a vaccine IMA-910, which contains some of the peptides of the present invention and describes the preparation of the vaccine using peptides in their salt form and their particle size.

The polynucleotide may be substantially pure, or contained in a suitable vector or delivery system. The nucleic acid may be may be DNA, cDNA, PNA, CNA, RNA or a combination thereof. Methods for designing and introducing such a nucleic acid are well known in the art. An overview is provided by e.g. S. Pascolo, Mol Med 2006, 127; 23-40; R. Stan, J D et al., Hematol Oncol Clin North Am 2006, 3; 613-636 or A Mandavi et al., Curr Oncol Rep 2006, 6, 465-472. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptide encoded by the nucleic acid may be a fusion protein, for example with an epitope that stimulates T-cells for the respective opposite CDR, as noted above.

The medicament of the invention may also include one or more adjuvants. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to 1018 ISS, aluminium salts, Amplivax, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA), ImuFact IMP321, Interferon-alpha or -beta, or pegylated derivatives thereof, IS Patch, ISS, ISCOMATRIX, ISCOMs, Juvlmmune, LipoVac, MALP2, MF59, monophosphoryl lipid A, Montanide IMS1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, PLG microparticles, resiquimod, SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Dupuis M et al. 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha, IFN-beta) (Gabrilovich et al. 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T-cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, Jun. 5, 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, Germany), which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera) Poly (I:C), such as AmpliGen, non-CpG bacterial DNA or RNA as well as immunoactive small molecules and antibodies such as cyclophosphamide, sunitinib, Bavacizumab, celebrex, NCX-4016, sildenafil, tadalafil, vardenafil, sorafinib, XL-999, CP-547632, pazopanib, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation.

Preferred adjuvants are dSLIM, BCG, OK432, ALDARA, PeviTer, and Juvlmmune.

Preferably medicaments of the present invention are active against cancer. The cancer may be non-metastatic or metastatic, in particular cancer of the buccal cavity and pharynx, cancer of the digestive tract, cancer of the colon, rectum, and anus, cancer of the respiratory tract, breast cancer, cancer of the cervix uteri, vagina, and vulva, cancer of the uterine corpus and ovary, cancer of the male genital tract, cancer of the urinary tract, cancer of the bone and soft tissue, and kaposi sarcoma, melanoma of the skin, eye melanoma, and non-melanoma eye cancer, cancer of the brain and central nervous system, cancer of the thyroid and other endocrine glands, Hodgkin Lymphoma, Non-Hodgkin Lymphoma, and myeloma. Most preferably the neoplastic disorder treated by the method of the current invention is colorectal cancer, lung cancer, breast cancer, pancreatic cancer, prostate cancer, gastric cancer, renal cancer, GIST or glioblastoma.

Since the peptides of the invention were isolated from glioblastoma, colorectal, pancreatic, lung, renal or gastric cancer, the medicament of the invention will be particularly useful if cancer to be treated is glioblastoma, colorectal, pancreatic, lung, renal or gastric cancer.

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of claimed tumor associated peptides (TAA or TUMAPs) on tissue biopsies can assist a pathologist in diagnosis of cancer. Detection of certain TUMAPs by means of antibodies, mass spectrometry or other methods known in the art can tell the pathologist that the tissue is malignant or inflamed or generally diseased. The presence of groups of TUMAPs can enable classification or subclassification of diseased tissues.

The detection of TUMAPs on a diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of TUMAPs shows that this mechanism is not exploited by the analyzed cells.

TUMAPs might be used to analyze lymphocyte responses against those TUMAPs such as T cell responses or antibody responses against the TUMAP or the TUMAP complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against TUMAPs can be considered in the assessment of side effects. Monitoring of lymphocyte responses might also be a valuable tool for follow-up examinations of transplantation therapies, e.g. for the detection of graft versus host and host versus graft diseases.

TUMAPs can be used to generate and develop specific antibodies against MHC/TUMAP complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

In addition, the peptides of the invention can be used to verify a pathologist's diagnosis of a cancer based on a biopsied sample.

The present invention includes a kit comprising: (a) a container that contains a pharmaceutical composition as described above, in solution or in lyophilized form; (b) optionally a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

For the purposes of the present invention, all references cited herein are incorporated by reference in their entireties.

EXAMPLES

Example 1

Identification of Tumour Associated Peptides (TUMAPS) Presented on Cell Surface

Tissue Samples

Patients' tumour and healthy tissues were provided by several different clinical sites (see Table below). Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol (Falk, K., et al. Nature 351, 290-296 (1991); Seeger, F. H. et al., Immunogenetics 49, 571-576 (1999)) using the HLA-A*02-specific antibody BB7.2 or the HLA-A, -B, —C-specific antibody W6/32, CNBr-activated sepharose, acid treatment and ultrafiltration.

Detection of TUMAPs by ESI-liquid Chromatography Mass Spectrometry (ESI-LCMS)

The obtained HLA peptide pools were separated according to their hydrophobicity by reversed-phase chromatography (CapLC, Waters) and the eluting peptides were analyzed in a hybrid quadrupole orthogonal acceleration time of flight tandem mass spectrometer (Q-TOF Ultima, Waters) equipped with an ESI source. Peptide pools were loaded onto a C18 pre-column for concentration and desalting. After loading, the pre-column was placed in line for separation by a fused-silica micro-capillary column (75 µm i.d.×250 mm) packed with 5 µm C18 reversed-phase material (Dionex). Solvent A was 4 mM ammonium acetate/water. Solvent B was 2 mM ammonium acetate in 80% acetonitrile/water. Both solvents were adjusted to pH 3.0 with formic acid. A binary gradient of 15% to 60% B within 90 minutes was performed, applying a flow rate of 5 µl/min reduced to approximately 200 nl/min by a split-system. A gold coated glass capillary (PicoTip, New Objective) was used for introduction into the micro-ESI source. The integration time for the TOF analyzer was 1.9 s with an interscan delay of 0.1 s. Subsequently, the peptide sequences were revealed by collisionally induced decay (CID) mass spectrometry (ESI-LCMS/MS). The identified TUMAP sequence was assured by comparison of the generated natural TUMAP fragmentation pattern with the fragmentation pattern of a synthetic sequence-identical reference peptide.

FIG. 1 and FIG. 2 show exemplary spectra obtained from tumour tissue for MHC class I associated TUMAPs (FIG. 1a-1h) and MHC class II associated TUMAPs (FIG. 2a-2f).

Example 2

Expression Profiling of Genes Encoding the Peptides of the Invention

The peptides identified as being presented on the surface of tumour cells by MHC molecules are likely able to induce T-cells with a high specificity of recognition for the tissue from which they were derived. In order to minimise the risk for autoimmunity induced by vaccination with such peptides the inventors focused on those peptides that are derived from proteins that are overexpressed on tumour cells compared to the majority of normal tissues.

The ideal peptide will be derived from a protein that is unique to the tumour and not present in any other tissue. To identify peptides that are derived from genes with an ideal expression profile, the identified peptides were assigned to the proteins and genes, respectively, from which they were derived and expression profiles of the genes were generated.

RNA Sources and Preparation

Surgically removed tissue specimens were provided by several different clinical sites (see Table 2) after written informed consent had been obtained from each patient.

Tumour tissue specimens were snap-frozen in liquid nitrogen immediately after surgery and later homogenized with mortar and pestle under liquid nitrogen. Total RNA was prepared from these samples using TRIzol (Invitrogen, Karlsruhe, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumour and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual). Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analysed with the GCOS software (Affymetrix), using default settings for all parameters. For normalization, 100 housekeeping genes provided by Affymetrix were used. Relative expression values were calculated from the signal log ratios given by the software and the normal sample was arbitrarily set to 1.0.

Expression profiles of all peptides of the present invention show a high expression of the respective gene in tumour tissue while being not or to a very low extend expressed in normal tissues.

Figure 1A:
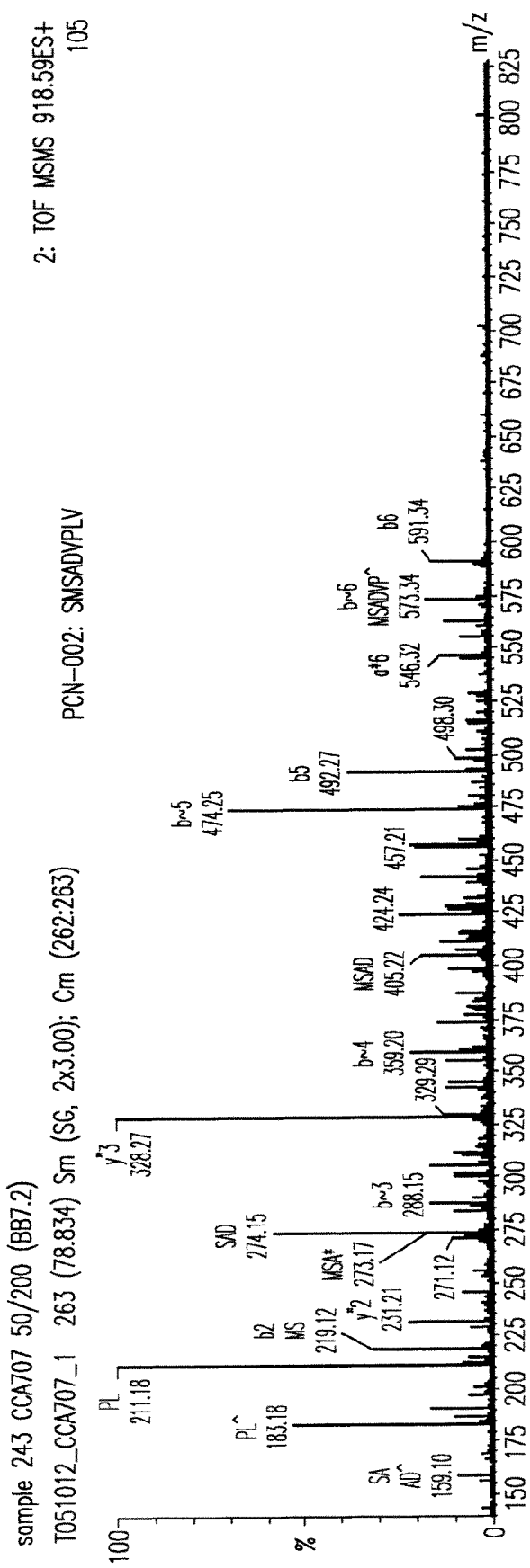
FIG. 1 shows the ESI-liquid chromatography mass spectra identifying tumour associated peptide (TUMAP) PCN-002 from colon carcinoma sample CCA707 (FIG. 1a), TOP-002 from glioblastoma sample GB 1006 (FIG. 1b), PTP-001 from glioblastoma sample GB 1006 (FIG. 1c), GAL-001 from renal cell carcinoma sample RCC 190 (FIG. 1d), CHI-001 from glioblastoma sample GB 1002 (FIG. 1e), JAK-001 from glioblastoma sample GB 1002 (FIG. 1f), AKR-001 from non-small cell lung cancer NSCLC-Pool 2 (FIG. 1g), and FNI-001 from pancreatic carcinoma sample PC330 (FIG. 1h) that were presented in a MHC class I restricted manner.
Figure 1B:
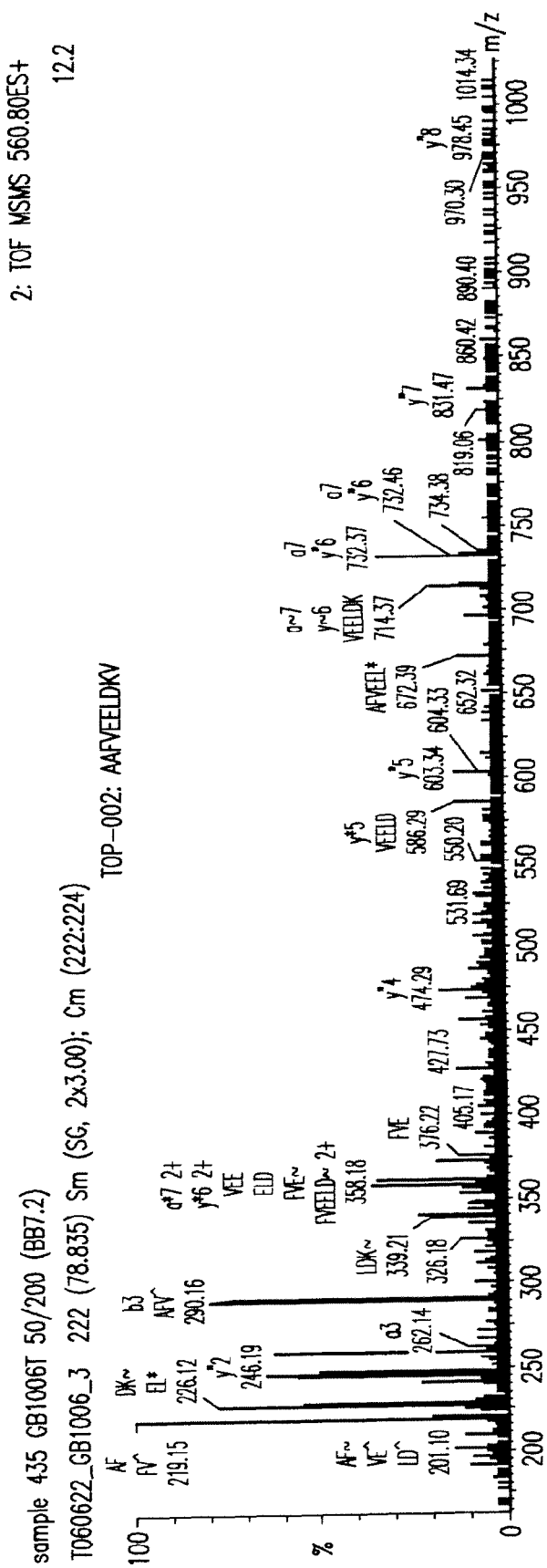
Figure 1C:
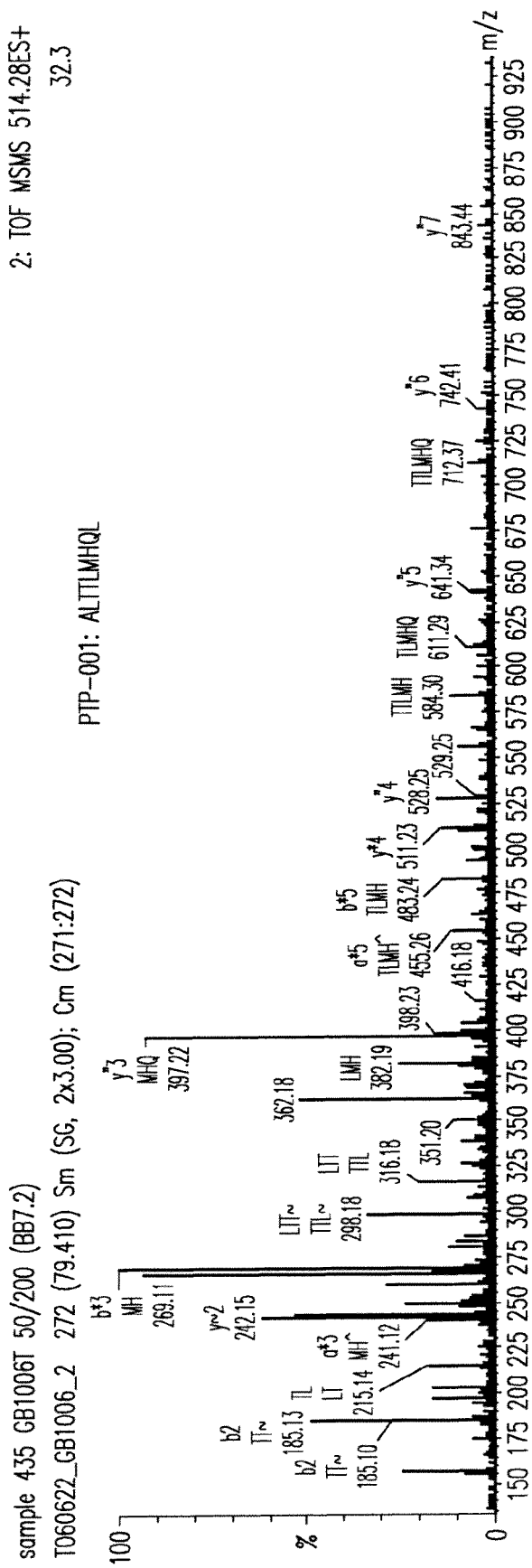
Figure 1D:
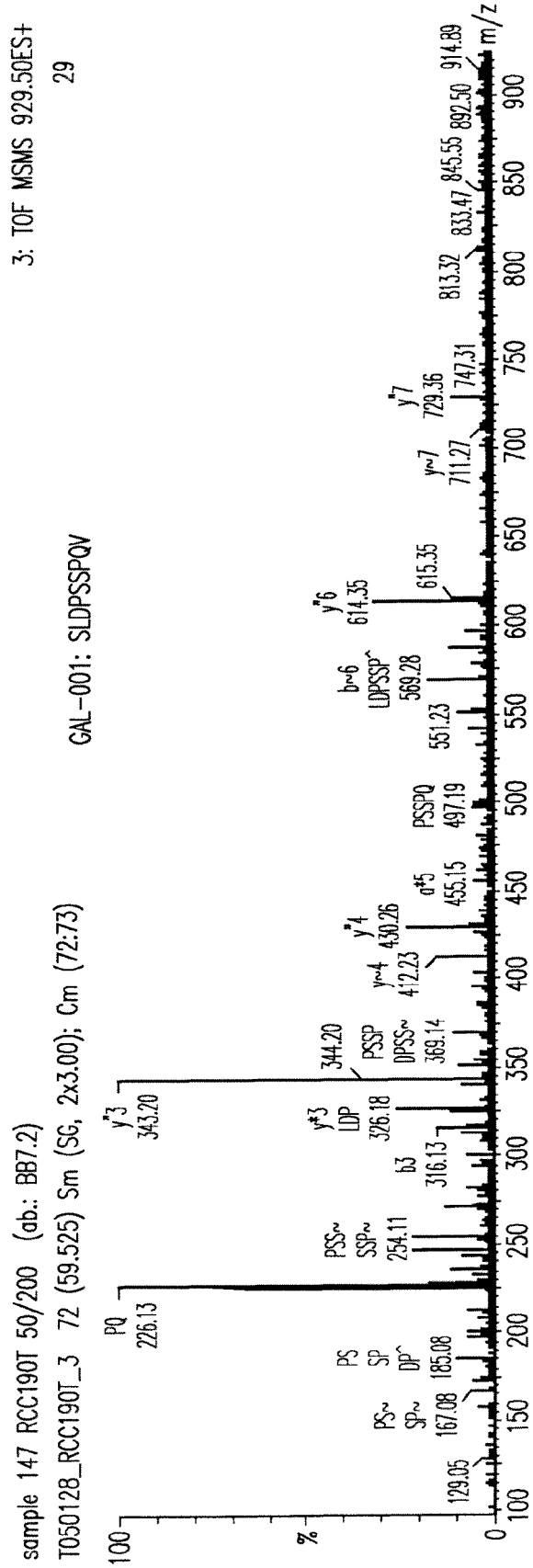
Figure 1E:
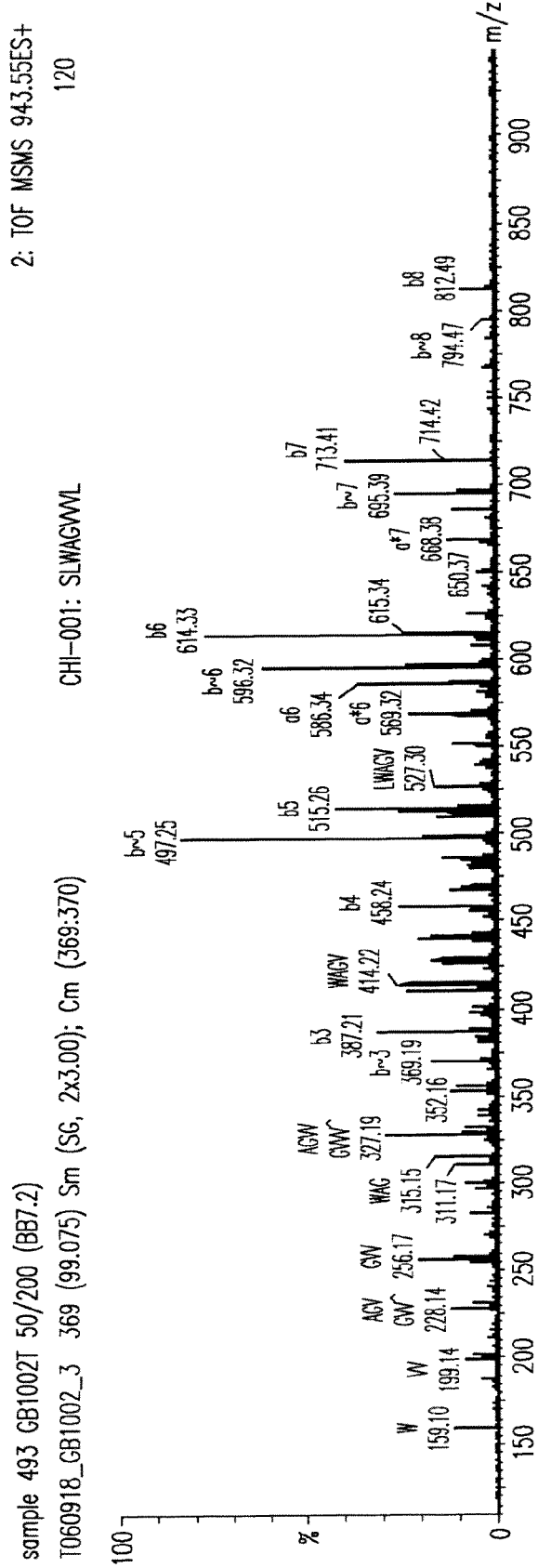
Figure 1F:
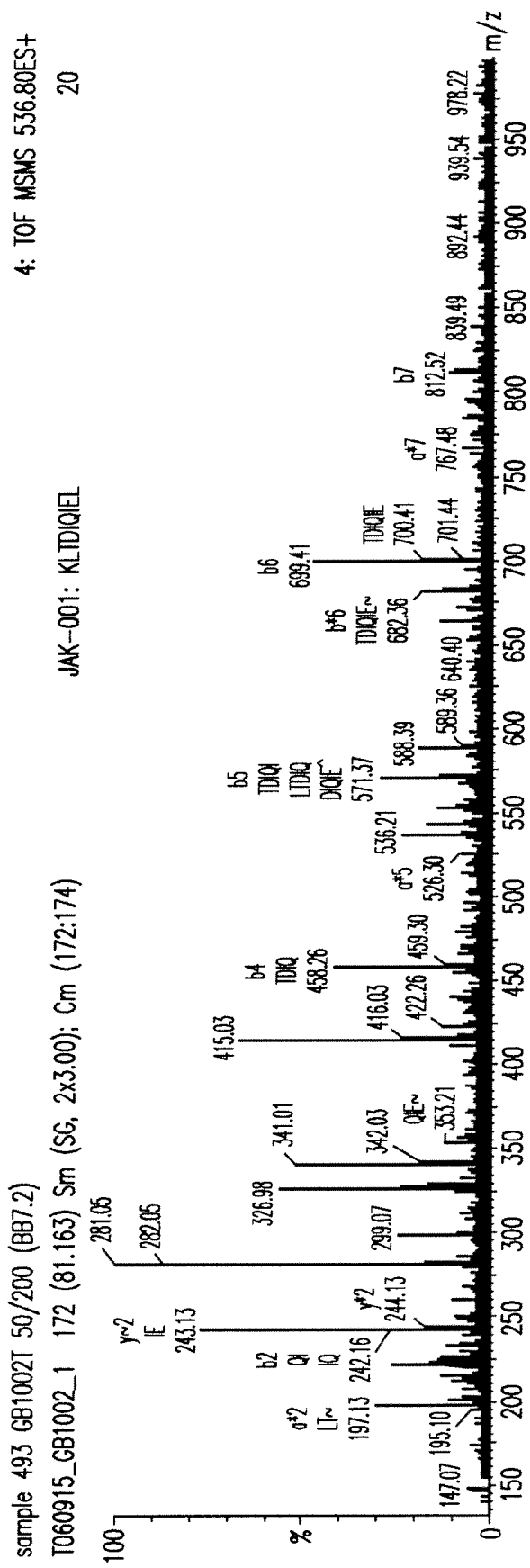
Figure 1G:
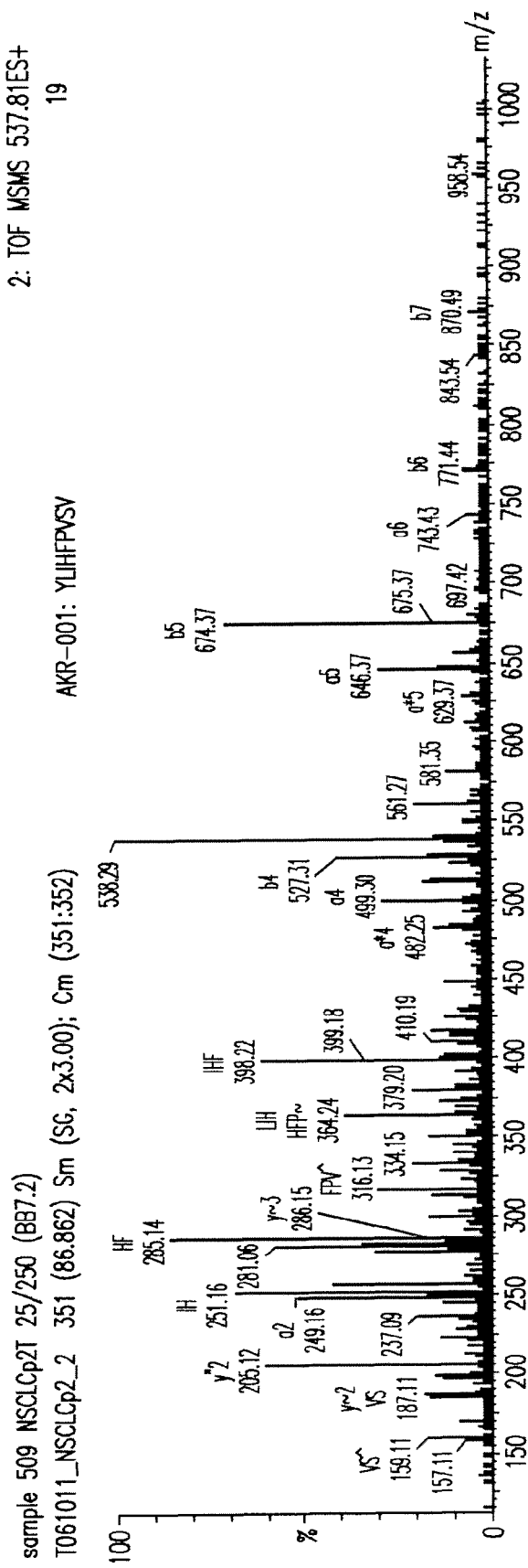
Figure 1H:
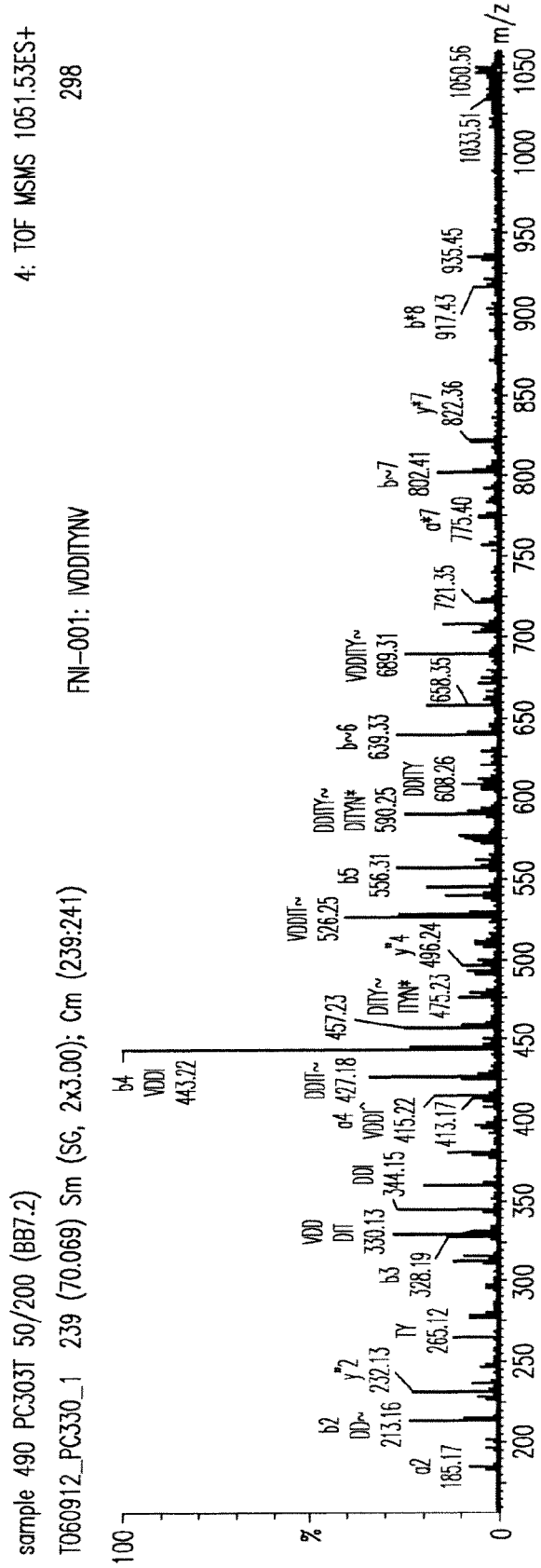
Figure 2A:
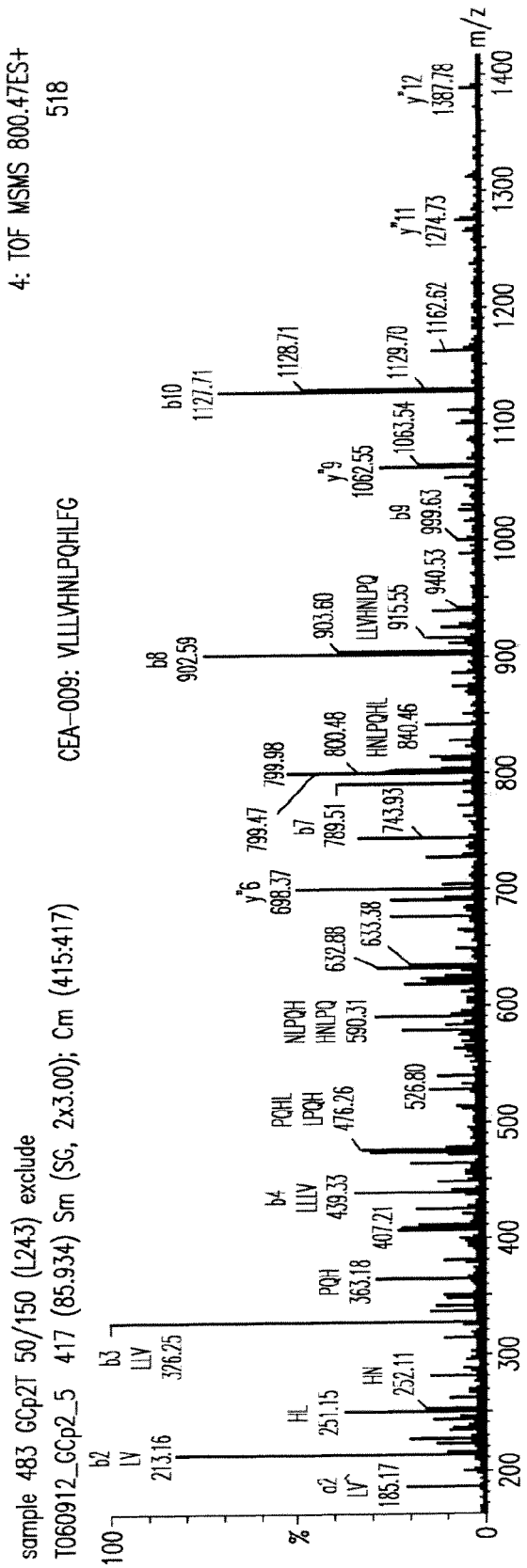
FIG. 2 shows the ESI-liquid chromatography mass spectra identifying tumour associated peptide (TUMAP) CEA-009 from gastric carcinoma GC-Pool 2 (FIG. 2a), TGFBI-006 from gastric carcinoma GC-Pool 1 (FIG. 2b), TGFBI-007 from glioblastoma sample GB6002 (FIG. 2c), TGFBI-008 from glioblastoma sample GB1004 (FIG. 2d), TGFBI-009 from non-small cell lung cancer NSCLC-Pool 1 (FIG. 2e), and TGFBI-010 from glioblastoma sample GB6002 (FIG. 2f) that were presented in a MHC class II restricted manner.
Figure 2B:
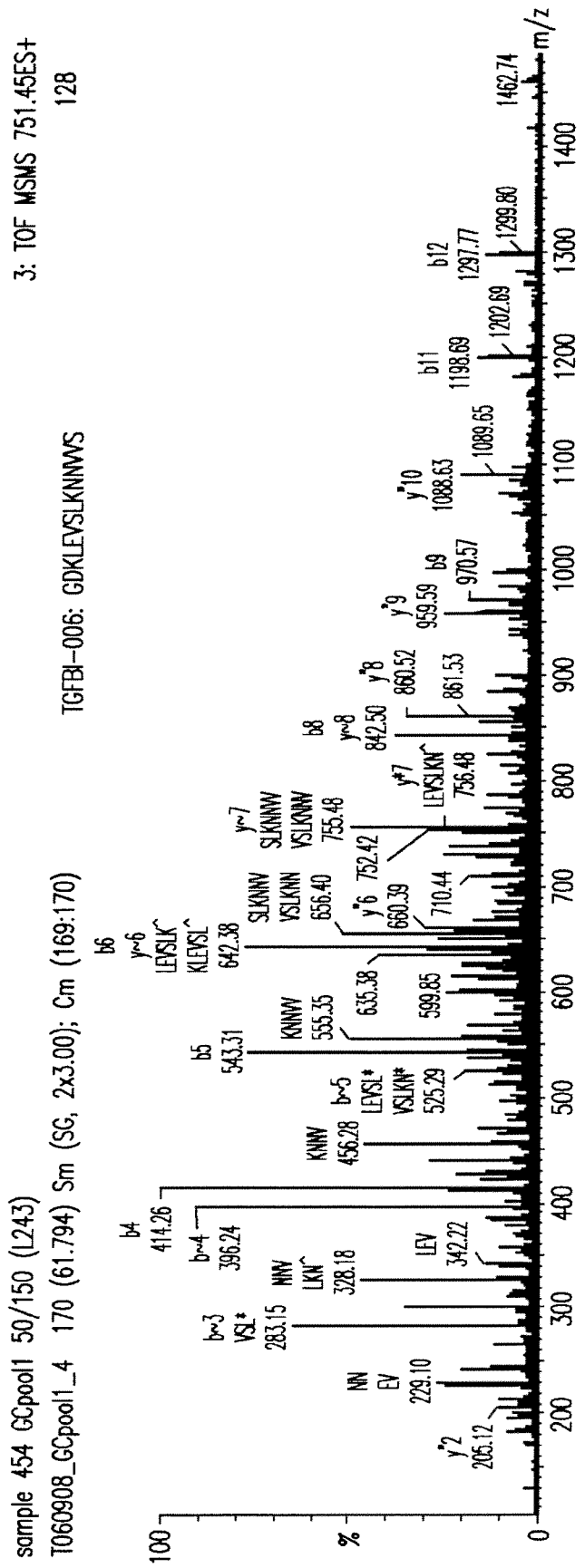
Figure 2C:
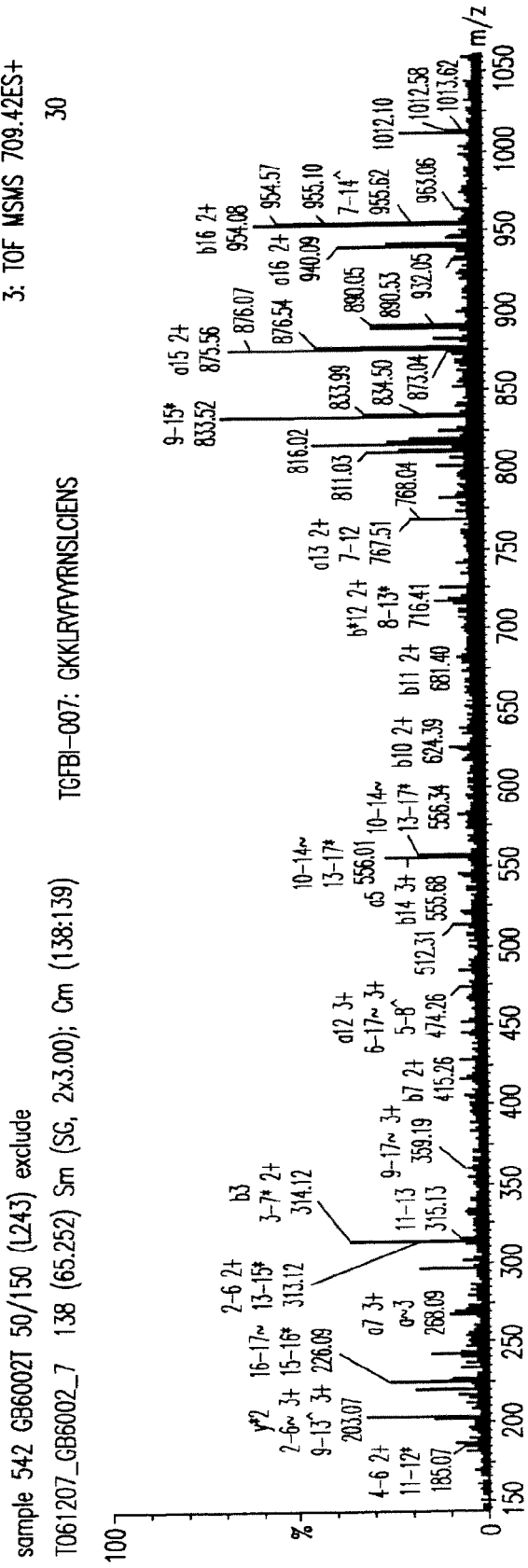
Figure 2D:
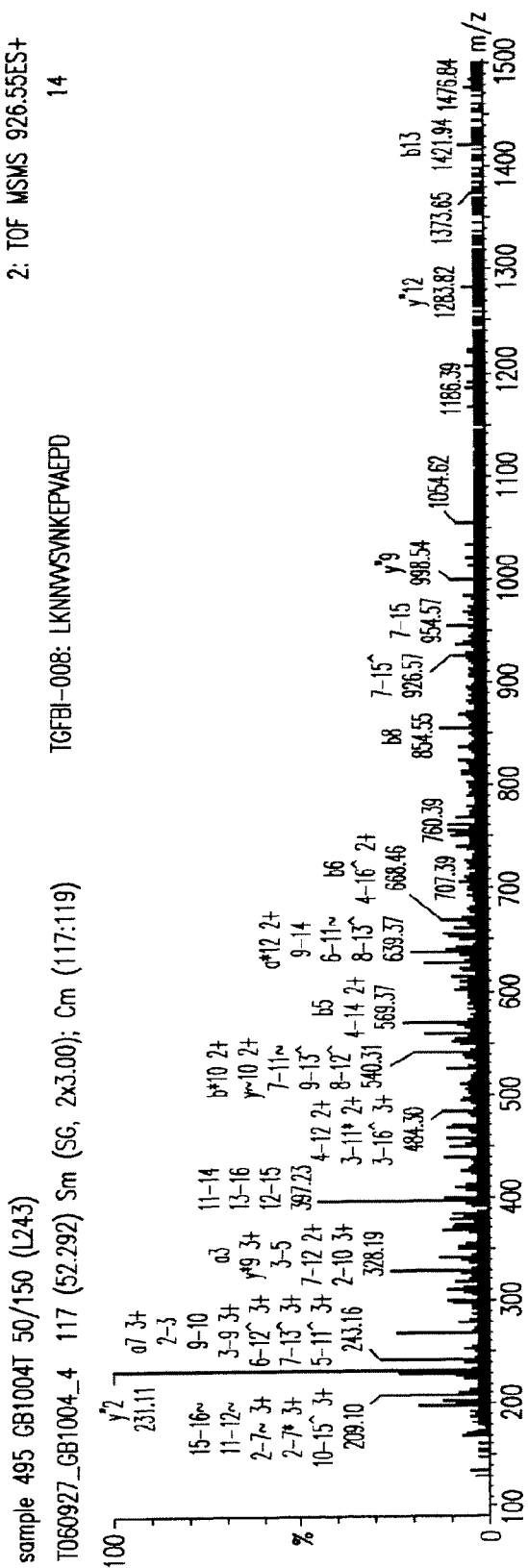
Figure 2E:
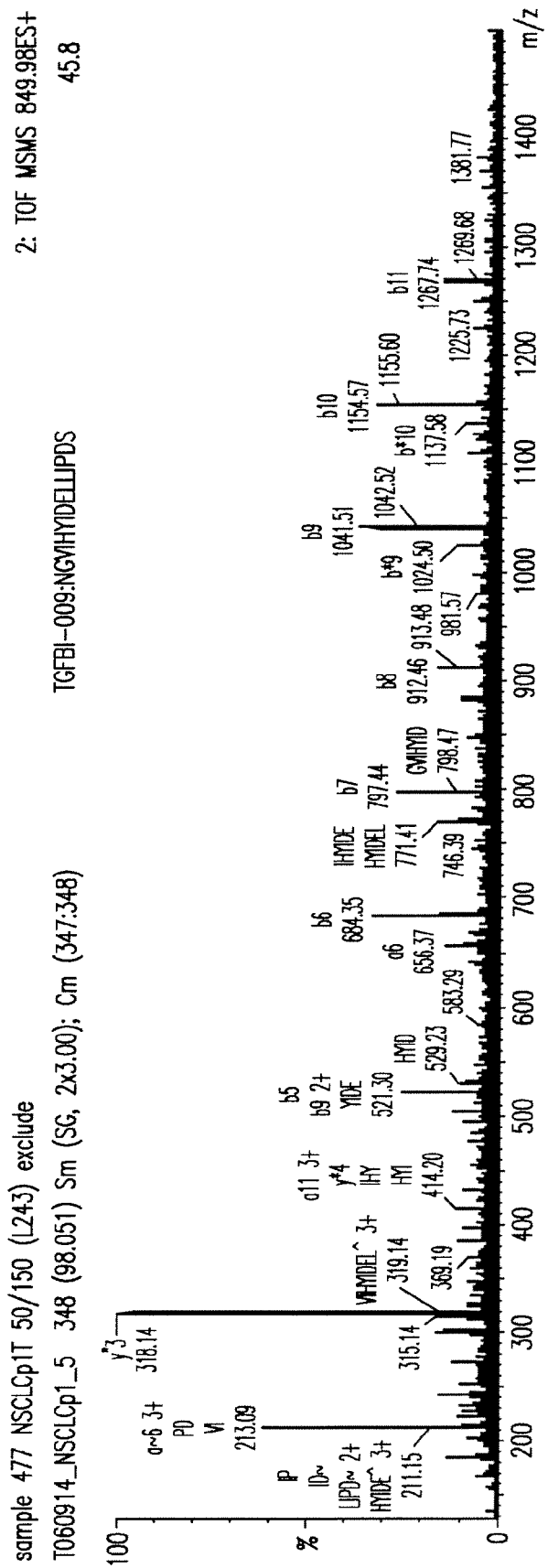
Figure 2F:
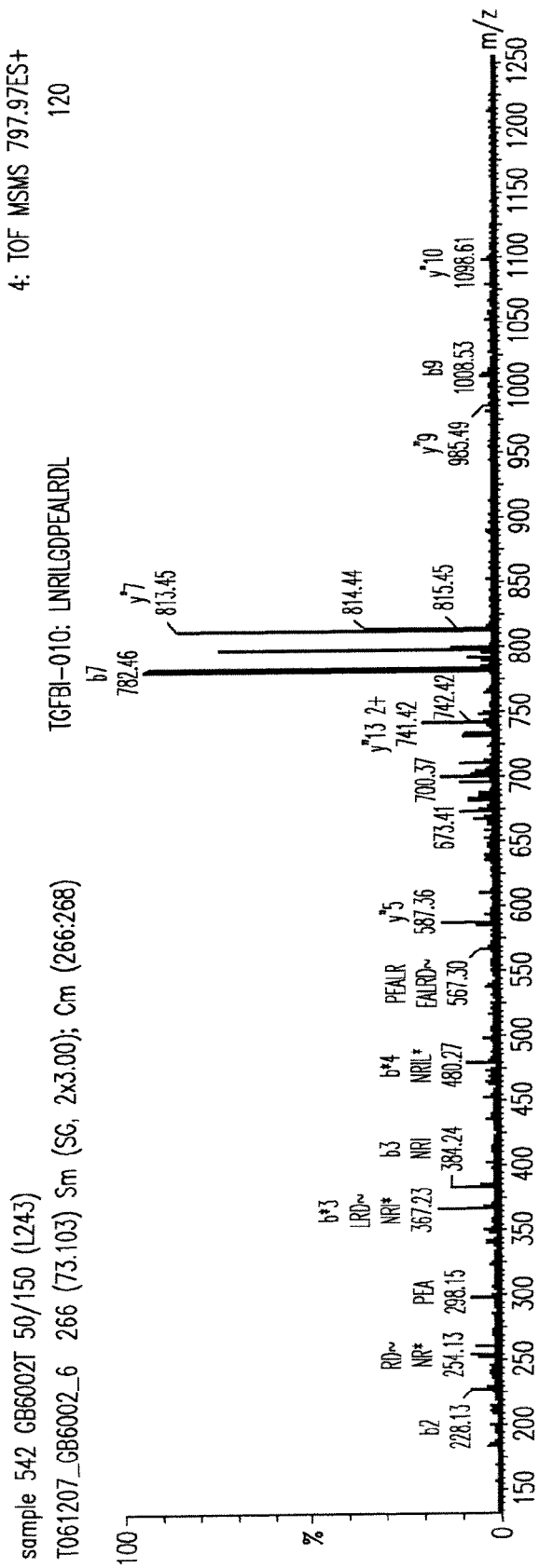
Figure 3A:
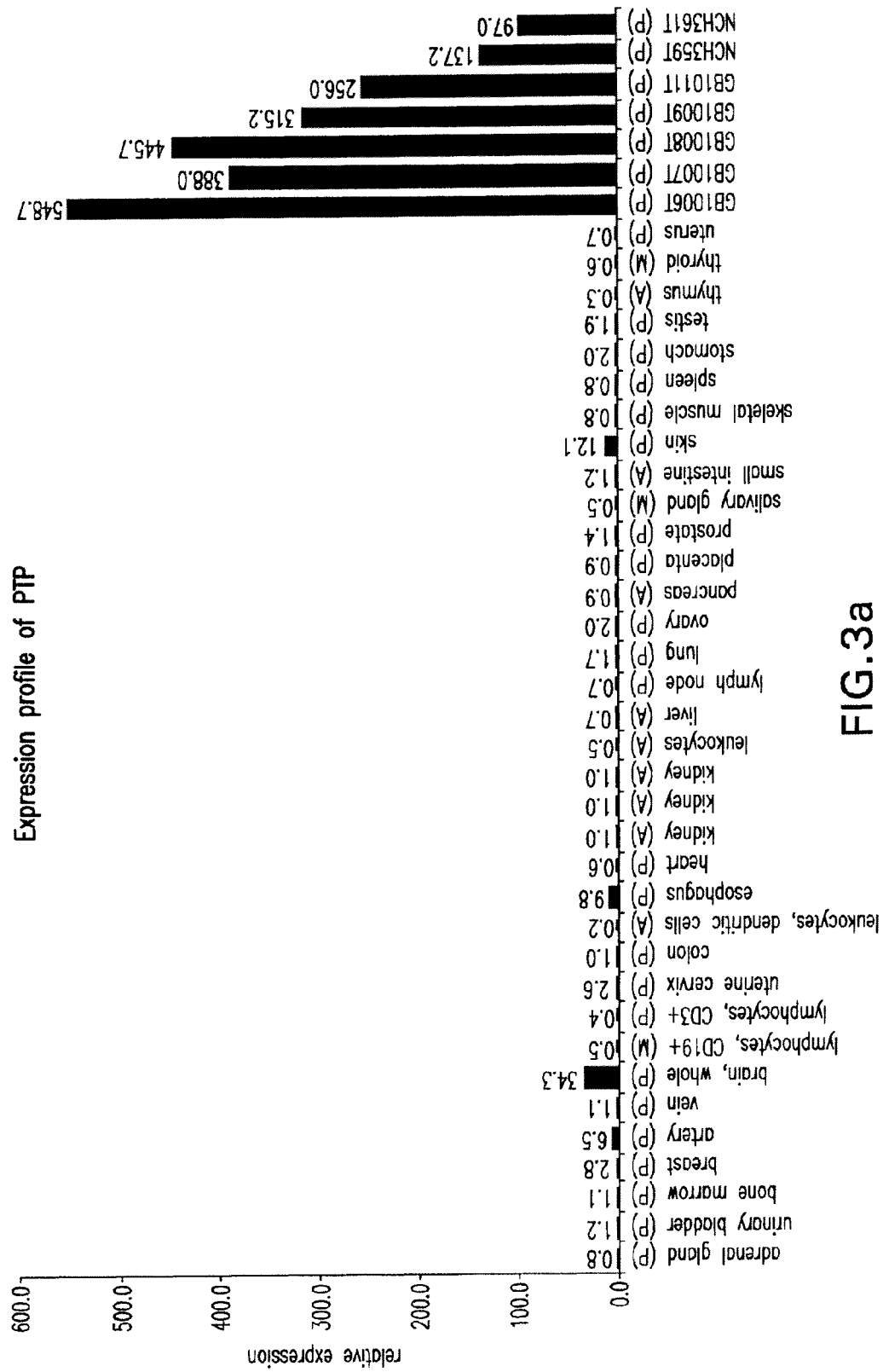
FIG. 3 depicts the expression profiles of two genes encoding glioblastoma associated peptides PTP-001 (FIG. 3a) and CHI-001 (FIG. 3b). Expression of the genes is absent or very low in normal tissues while increased up to more than 250-fold in glioblastoma samples (GB1006T to GB1011T; NCH359T and NCH361T).
Figure 3B:
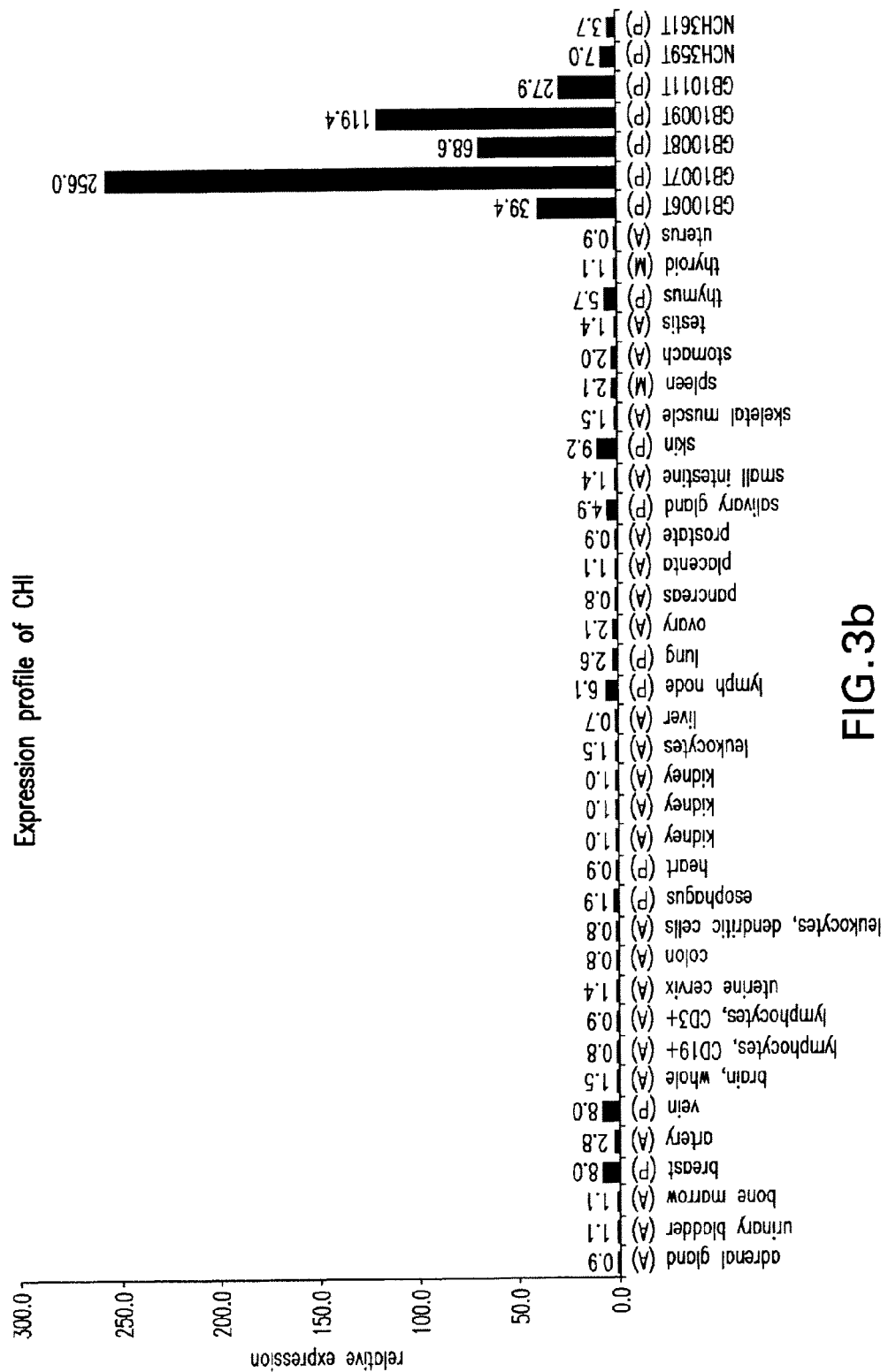

FIG. 3 shows such profiles for the genes of glioblastoma specific peptides PTP-001 (gene: PTPRZ1, FIG. 3a), and CHI-001 (gene: CH3L2, FIG. 3b).

Example 3

Re-Detection of Identified TUMAPs by ESI-Liquid Chromatography Mass Spectrometry (ESI-LCMS) in Additional Tumour Samples TUMAPs identified by the method of EXAMPLE 1 were systematically searched for on colorectal tumour samples by mass spectrometry.

The obtained HLA peptide pools were separated according to their hydrophobicity by reversed-phase chromatography (CapLC, Waters) and the eluting peptides were analyzed in a hybrid quadrupole orthogonal acceleration time of flight tandem mass spectrometer (Q-TOF Ultima, Waters) equipped with an ESI source. Peptide pools were loaded onto a C18 pre-column for concentration and desalting. After loading, the pre-column was placed in line for separation by a fused-silica micro-capillary column (75 μm i.d.×250 mm) packed with 5 μm C18 reversed-phase material (Dionex). Solvent A was 4 mM ammonium acetate/water. Solvent B was 2 mM ammonium acetate in 80% acetonitrile/water. Both solvents were adjusted to pH 3.0 with formic acid. A binary gradient of 15% to 60% B within 90 minutes was performed, applying a flow rate of 5 μl/min reduced to approximately 200 nl/min by a split-system. A gold coated glass capillary (PicoTip, New Objective) was used for introduction into the micro-ESI source. The integration time for the TOF analyzer was 1.9 s with an interscan delay of 0.1 s. For detection of defined peptides high sensitive screening was performed in this type of ESI-LCMS experiments on the basis of known molecular weights and retention times of the peptides in the chromatographic system. Therefore, a list containing the m/z values of the previously identified peptides (singly and/or doubly charged) was applied for precursor selection. Subsequently, the sequence was revealed by collisionally induced decay (CID) mass spectrometry (ESI-LCMS/MS). The TUMAP sequence was confirmed by comparison of the generated natural TUMAP fragmentation pattern with the fragmentation pattern of a synthetic sequence-identical reference peptide. Evaluation of the HLA peptide purification yield and reproducibility of the analytical system, including retention time stability was carried out using the intensity and retention time of an abundant endogenous HLA-A*02 peptide (YLL-PAIVHI derived from DDX5) as internal standard. Therefore, the CRC sample inclusion criterion for detection of previously identified TUMAP in these experiments was set to a minimal intensity of 650 counts per scan of the internal doubly charged standard signal (YLLPAIVHI) in the LCMS/MS experiment to assure a successful HLA peptide isolation and the correct performance of the analytical system.

Table 2 shows the results of an analysis of colon and rectum cancer samples of different stages as well as metastases originating from either primary tumour site. All HLA-A*02 TUMAPs were found on the majority of samples. Re-detection frequencies of HLA-DR TUMAPs are generally lower. This can be expected because for HLA class II peptides, several length variants for each core sequence may exist. ODC-001, a TUMAP identified previously (M Diehl, PhD thesis 1998, University of Tuebingen) and known to be presented on a large number of colon tumours served as positive control.

TABLE 2

Re-detection of TUMAPS in CRC samples

| | | | TUMAP re-detected (+) or not detected (−) | | | | | | |
|---|---|---|---|---|---|---|---|---|---|
| | | | class I | | | | | | class II |
| CRC No | Tumor sample | Tumor location | Tumor stage | C20-001 | TGFBI-001 | TOP-001 | NOX-001 | PCN-001 | ODC-001 | TGFBI-004 |
|---|---|---|---|---|---|---|---|---|---|
| 1 | CCA062 | colon | I | n.a. | n.a. | n.a. | n.a. | n.a. | n.a. | − |
| 2 | CCA740 | colon | II | + | + | + | + | + | + | n.a. |
| 3 | CCA165 | colon | II | + | + | + | + | + | + | − |
| 4 | CCA712 | colon | III | + | + | + | − | − | + | n.a. |
| 5 | CCA707 | colon | III | + | + | + | + | + | + | n.a. |
| 6 | CCA718 | colon | III | + | + | + | + | + | + | n.a. |
| 7 | CCA739 | colon | III | + | + | + | + | + | + | n.a. |
| 8 | CCA166 | colon | III | + | + | + | + | + | + | − |
| 9 | CCA734 | colon | III | + | + | + | + | + | + | n.a. |
| 10 | CCA719 | colon | IV | + | + | + | + | − | + | n.a. |
| 11 | CCA725 | colon | IV | + | + | + | − | + | + | n.a. |
| 12 | CCA164 | colon | IV | + | + | − | − | + | + | − |
| 13 | CCA167 | colon | IV | n.a. | n.a. | n.a. | n.a. | n.a. | n.a. | − |
| 14 | CCA056 | colon | ? | n.a. | n.a. | n.a. | n.a. | n.a. | n.a. | − |
| 15 | CCA305 | colon | ? | n.a. | n.a. | n.a. | n.a. | n.a. | n.a. | − |
| 20 | CCA708 | colon metastasis | IV | + | + | + | + | + | + | + |
| 16 | CCA160 | rectum | II | + | + | + | + | + | + | + |
| 17 | CCA754 | rectum | II | + | + | + | − | + | + | n.a. |
| 18 | CCA170 | rectum | III | n.a. | n.a. | n.a. | n.a. | n.a. | n.a. | + |
| 19 | CCA171 | rectum | IV | n.a. | n.a. | n.a. | n.a. | n.a. | n.a. | − |
| 21 | CCA724 | rectum metastasis | IV | + | + | − | − | − | + | + |
| Detected in % of analyzed samples | | | | 100% | 100% | 87% | 67% | 80% | 100% | 33% | n.a.: not analysed

Example 4

Binding of HLA Class I-Restricted Peptides to HLA-A*0201

The HLA binding assay was performed using the ELISA EpI Kit (obtained from Sceren Buus, Institute of Medical Microbiology and Immunology at the University of Copenhagen, Denmark) according to Sylvester-Hvid (Sylvester-Hvid, at al., 2002, Tissue Antigens, 59, 251-258) and the ELISA EpI Kit manual by the manufacturer.

Preparation of Peptide Solutions

Peptides were dissolved in DMSO+0.5% TFA (Merck, Darmstadt, Germany) at a concentration of 10 mg/ml. The highest peptide working solution used in this assay was 200 µM, therefore the stock solution was diluted 1:50 in a peptide-dilution buffer (PBS with 0.1% Lutrol-F68 and 10 mg/l Phenol red) to a final volume of 100 µl. A serial five-fold dilution was performed with peptide-dilution buffer.

Refolding of HLA-A*0201/Peptide Complexes

According to the manual, a 2-fold concentrated HLA-A*0201 solution was prepared by mixing 3× pH buffer (pH 6.6), Lutrol-F68, human β2m, recombinant HLA-A*0201 (all included in the ELISA EpI Kit) with PBS.

For the refolding process, 15 µl of peptide serial dilutions and 15 µl of the 2-fold concentrated MHC mix were mixed in 96-well plates (Nunc, Rochester, N.Y., USA) and incubated at 18° C. for 48 hours.

Quantification of the Complexes by an ELISA

Maxisorp plates (Nunc, Rochester, N.Y.) were coated with 5 µg/ml w6/32 antibody in coating buffer (pH 9.6), incubated for 24 h at 4° C. and blocked with 5% skim milk powder (Merck, Darmstadt, Germany) in PBS over night at 4° C.

Figure 4:
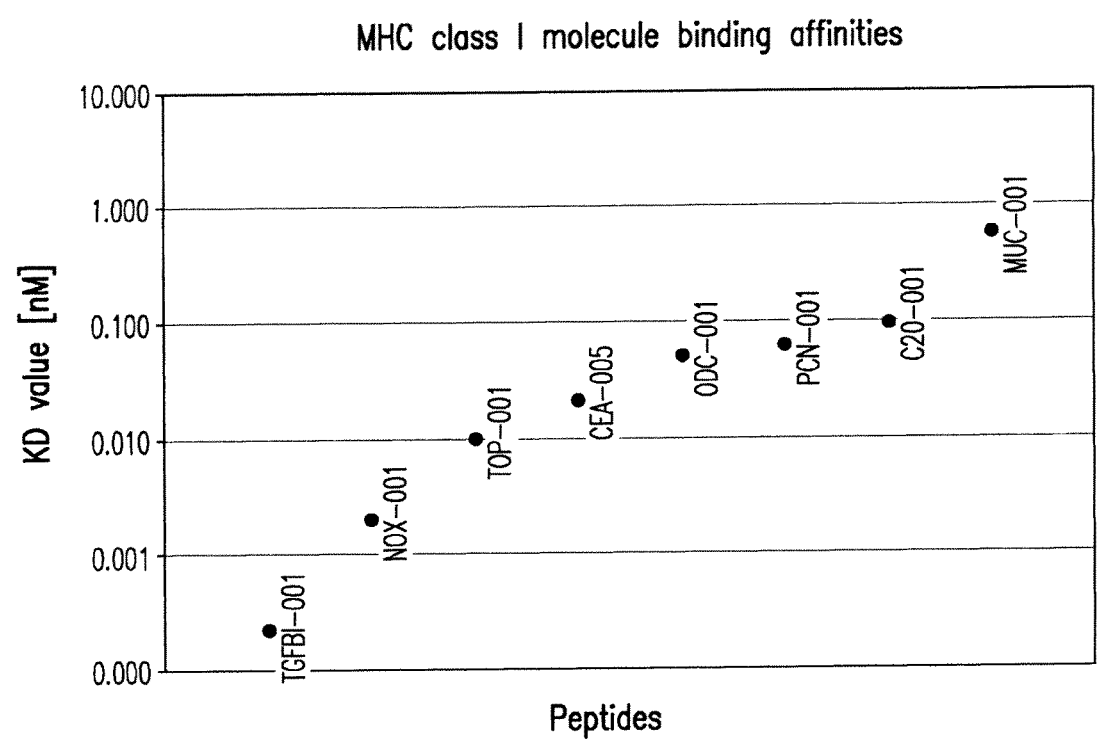
FIG. 4 depicts binding affinities of selected peptides to HLA-A*0201 as measured by EpI ELISA according to Sylvester-Hvid, C, et al., 2002, Tissue Antigens, 59, 251-258). The analysis was limited to peptides known to be MHC class I binding peptides. Affinities of HLA-DR binding peptides cannot be measured with this assay.

MHC complex standard (ELISA EpI Kit) was diluted with 2% skim milk powder in PBS (SMP/PBS) to a concentration of 10 nM. A serial 3.16-fold dilution was prepared and transferred to the coated and blocked Maxisorp plate. The peptide-MHC complexes were diluted 10-fold with 2% SMP/PBS, transferred to the same Maxisorp plate and incubated for 2 hours at 4° C. Rabbit anti-hβ2m antibody (ELISA EpI Kit) was added in a 1:2500 dilution in 2% SMP/PBS and incubated for 1 hour at 4° C. Amplification buffer (HRP-conjugated goat anti-rabbit polymer) and mouse serum (both supplied with the ELISA EpI Kit) was diluted in 2% SMP/PBS, added to the plates and incubated 30 minutes at room temperature. Development buffer (Tetramethylbenzidine, TMB; ELISA EpI Kit) was added, plates were incubated under light protection for 30 minutes at room temperature. The reaction was stopped by adding 0.2 M sulfuric acid (VWR, Darmstadt, Germany). Plates were read at OD450 nm using the VERSAmax ELISA-Reader (Molecular Devices, Sunnyvale, Calif., USA). Data were interpreted with Excel and Prism®, Graphpad 3.0. Results are shown in FIG. 4. A lower KD value reflects higher affinity to HLA-A*0201. Binding affinities stretch over a range of approximately four decades but most peptides have similar binding affinities within one decade (C20-001, ODC-001, PCN-001, TOP-001). The affinity of MUC-001 is about one decade lower compared to the majority of the included ligands but MUC-001 was nevertheless able to induce a T-cell response when used in a vaccine for renal carcinoma (Wierecky, J, et al., 2006, Cancer Res., 66, 5910-5918). On the other hand, NOX-001 has a slightly higher binding affinity and TGFBI-001 is the strongest binder with a 100-fold lower KD value compared with the majority of peptides.

In absolute terms, KD values between 0.01 and 0.1 nM as observed for the majority of peptides represent already a strong binding. Similar affinities had been also observed for peptides contained in the renal cell carcinoma vaccine IMA901 that was successfully tested (H. Singh-Jasuja, et al., ASCO Meeting 2007 Poster #3017; M. Staehler, et al., ASCO meeting 2007; Poster #3017). Therefore, binding properties of peptides of the present invention are quite similar to those of peptides that have been shown in vivo to induce a T-cell response.

Example 5

In Vitro Immunogenicity of MHC Class I Presented Peptides

In Vitro Priming of CD8+ T Cells

To perform in vitro stimulations by artificial antigen presenting cells (aAPC) loaded with peptide-MHC complex (pMHC) and anti-CD28 antibody, first PBMCs (peripheral blood mononuclear cells) were isolated from fresh HLA-A*02+ buffy coats by using standard density gradient separation medium (PAA, Cölbe, Germany). Buffy coats were either obtained from the Blood Bank Tubingen or from the Katharinenhospital Stuttgart. Isolated PBMCs were incubated overnight in T-cell medium (TCM) for human in vitro priming consisting of RPMI-Glutamax (Invitrogen, Karlsruhe, Germany) supplemented with 10% heat inactivated human AB serum (PAA, Cölbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Obtained CD8+ T-cells were incubated until use in TCM supplemented with 2.5 ng/ml IL-7 (PromoCell, Heidelberg, Germany) and 10 U/ml IL-2 (Chiron, Munich, Gemany). Generation of pMHC/anti-CD28 coated beads, T-cell stimulations and readout was performed as described before (Walter, S, et al., 2003, J. Immunol., 171, 4974-4978) with minor modifications. Briefly, biotinylated recombinant HLA-A*0201 molecules lacking the transmembrane domain and being biotinylated at the carboxy terminus of the heavy chain were produced following a method described by (Altman, J D, et al., 1996, Science, 274, 94-96). The purified costimulatory mouse IgG2a anti human CD28 Ab 9.3 (Jung, G, Ledbetter, J A, and Muller-Eberhard, H J; 1987, Induction of cytotoxicity in resting human T lymphocytes bound to tumor cells by antibody heteroconjugates, Proc Natl Acad Sci USA, 84, 4611-4615) was chemically biotinylated using Sulfo-N-hydroxysuccinimidobiotin as recommended by the manufacturer (Perbio, Bonn, Germany). Beads used were 5.60 µm large streptavidin coated polystyrene particles (Bangs Laboooratories, Illinois/USA). pMHC was used as positive control and negative controls were A*0201/MLA-001 (peptide ELAGIGILTV from modified Melan-A/MART-1) and A*0201/DDX5-001 (YLL-PAIVHI from DDX5) or A*0201/HBV-001 (FLPSDFFPSV), respectively.

800,000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). Stimulations were initiated in 96-well plates by conincubating 1×10$^6$ CD8+ T cells with 2×10$^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubation was continued for 3-4 days at 37° C. This stimulation cycle was performed for a total of three times. Finally, tetrameric analyses were performed with fluorescent MHC tetramers (produced as described by (Altman, J D, et al., 1996, Science, 274, 94-96)) plus antibody CD8-FITC clone SK1 (BD, Heidelberg, Germany) on a four-color FACSCalibur (BD). Peptide specific cells were calculated as percentage of total CD8+ T cells. Evaluation of tetrameric analysis was performed using the software FCS Express (De Novo Software). In vitro priming of specific tetramer+CD8+ lymphocytes was detected by appropriate gating and by comparison to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations).

Figure 5:
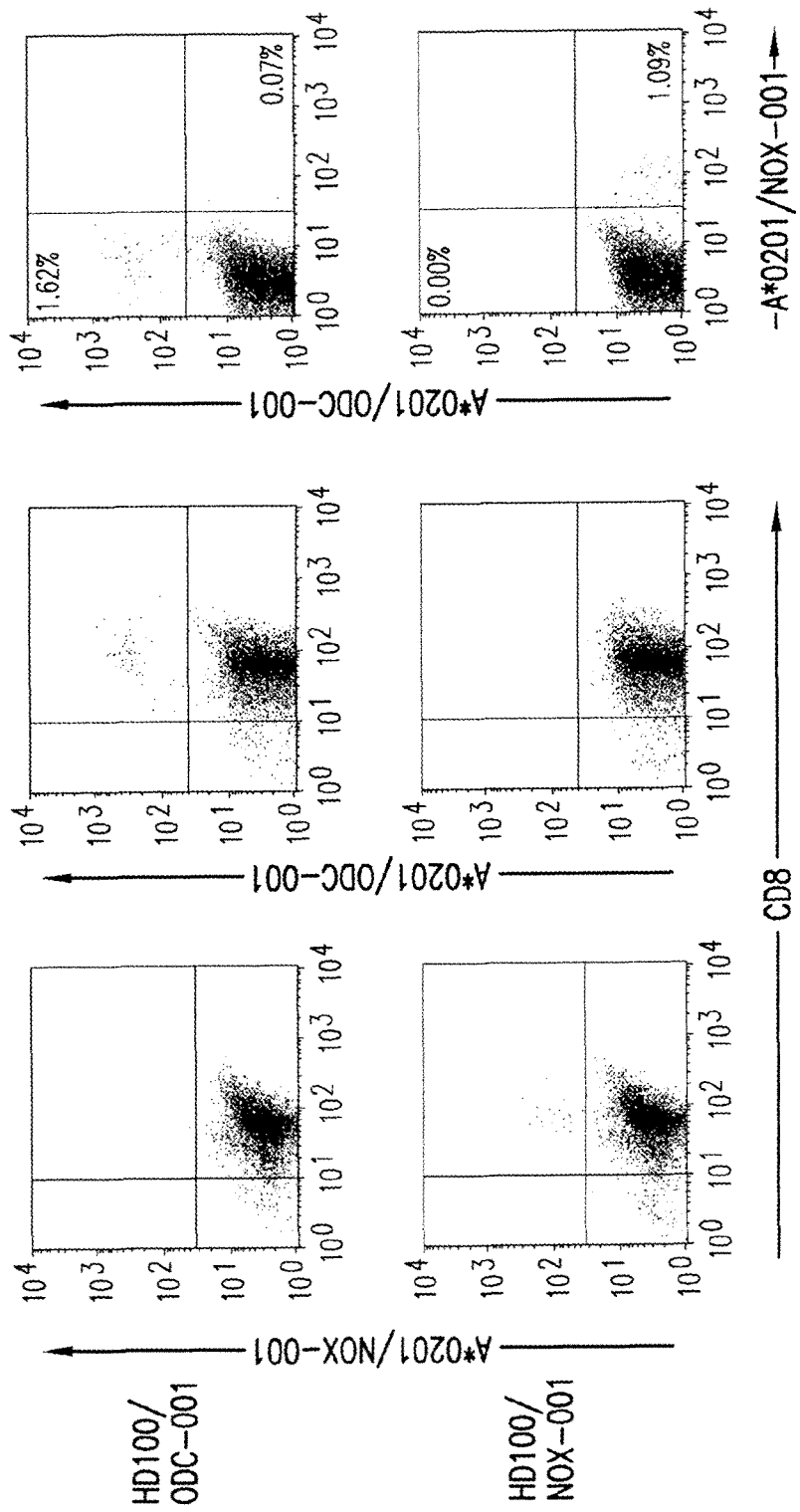
FIG. 5 depicts the Tetramer analysis of microsphere driven proliferation of ODC-001 and NOX-001 specific CD8+ lymphocytes from peripheral blood. $1 \times 10^6$ CD8+ enriched PBMCs per well of the healthy HLA-A*0201+ donor HD100 was stimulated weekly with microspheres coupled to anti-CD28 plus high density tumor antigen A*0201/ODC-001 (upper panel) or anti-CD28 plus high density tumor antigen A*0201/NOX-001 (lower panel). After three stimulations in vitro, all cells were stained with antibody CD8 FITC plus tetramers A*0201/NOX-001 PE and A*0201/ODC-001 APC. Cells are gated on the lymphocyte population or CD8+ lymphocytes (right panel) and numbers represent percentage of tetramer+ within CD8+ lymphocytes.

Peptides of the present invention were tested together with peptides of known in vivo immunogenicity for comparison. A representative staining showing generation of T-cell lines specific for NOX-001 and ODC-001 is shown in FIG. 5. The results are summarized in table 3 below. The CEA-005 peptide that was optimised for in vitro T-cell induction (Fong, L, et al., 2001, J. Immunol., 166, 4254-4259) served as control. All peptides showed in vitro immunogenicity in the PBMCs of healthy donors.

TABLE 3

In vitro immunogenicity of peptides of the invention compared with those of vaccine peptides

| Antigen | Immunogenicity detected |
|---|---|
| TGFBI-001 | yes |
| NOX-001 | yes |
| PCN-001 | yes |
| TOP-001 | yes |
| C20-001 | yes |
| ODC-001 | yes |
| CCN-001 | yes |
| PTP-001 | yes |
| CHI-001 | yes |
| JAK-001 | yes |

Table 4 provides additional in vitro immunogenicity data:

| Antigen | Positive donors/donors tested | Positive wells/wells tested |
|---|---|---|
| IMA-HBV-001 | 7/16 (44%) | 10/107 (9%) |
| IMA-TGFBI-001 | 3/4 (75%) | 4/22 (18%) |
| IMA-NOX-001 | 3/5 (60%) | 9/60 (15%) |
| IMA-PCN-001 | 3/4 (75%) | 4/42 (10%) |
| IMA-TOP-001 | 2/5 (40%) | 7/72 (10%) |
| IMA-C20-001 | 1/5 (20%) | 1/60 (2%) |
| IMA-ODC-001 | 1/5 (20%) | 1/60 (2%) |
| IMA-HBV-001 | 2/5 (40%) | 10/54 (19%) |
| IMA-CEA-004 | 4/4 (100%) | 50/60 (83%) |
| IMA-CCN-001 | 5/5 (100%) | 42/54 (78%) |
| IMA-MET-001 | 4/6 (67%) | 30/72 (42%) |

Results of in vitro immunogenicity experiments conducted by immatics are summarised here. Results shown have been obtained by stimulation of CD8+ cells with high density beads. As different human serum lots may highly affect the immunogenicity results, only assays in which one and the same serum lot was used, were evaluated together.

Example 6

In Vitro Immunogenicity for MHC Class II Presented Peptides

T helper cells play an important role in supporting CTLs to activate and sustain immune responses against tumor cells. Therefore, MHC class II peptides were included in IMA910. TGFBI-004, one of the three class II peptides contained in IMA910, was tested for its immunogenic potential in vitro and proved to be an inducer of both specific CD4+ and CD8+ T cells. The generation of CD4+ and functional CD8+ T lymphocytes was shown in experiments using stimulations performed in an autologous system.

Principle of Test

Priming and expansion of specific human CD4+ and CD8+ cells were assayed in vitro by priming of monocyte-depleted PBMCs with autologous DCs and restimulation with autologous PBMCs. Briefly, to generate antigen-specific CD4+ T cells, monocyte-depleted PBMCs of one healthy donor (HLA genotype class I: A1/A25/B8/B18 and class II: DQB1*02/DQB1*06/DRB1*03/DRB1*15/DRB3/DRB5) were stimulated using peptide-pulsed autologous DCs and restimulated with autologous PBMCs plus peptide. As a read-out system, IFNγ production upon short term restimulation was assessed by ELISPOT and flow cytometry. T cells were analysed after eight stimulations by ELISPOT and intracellular IFNγ staining plus CD4-FITC and CD8-PerCP to determine the percentage of IFNγ-producing cells in specific T-cell subpopulations. In this experiment, cells stimulated with TGFBI-004 peptide from different wells were pooled, incubated with irrelevant peptide for the read-out and performed as negative controls.

Generation of Dendritic Cells (DCs)

Human DCs were obtained from monocytes cultured in DC medium consisting of RPMI 1640-Glutamax/25 mM Hepes (Invitrogen, Germany) supplemented with 10% autologous plasma//100 U/ml penicillin and 100 µg/ml streptomycin. First, buffy coat and plasma was obtained by centrifugation of the blood from a healthy donor (Bloodbank Tubingen). PBMCs were then isolated from the buffy coat by standard density gradient separation (Lymphocyte Separation Medium, PAA, Austria) and resuspended in DC medium to determine total cell number. 100-120 Million of PBMCs were washed, resuspended in 15 ml X-Vivo 20 medium (BioWhittaker, Belgium) and transferred to a cell culture flask. After 2 hours at 37° C., media containing peripheral blood leukocytes (PBL) was removed, adherent monocytes were washed twice with 10 ml PBS and cultured for 6 days in 10 ml DC medium with 100 ng/ml GM-CSF and 30 ng/ml IL-4 (ImmunoTools, Germany) or 20 ng/ml (R&D systems, Germany). On day 3 and 5, 100 ng/ml GM-CSF and 30 ng/ml IL-4 (Immunotools) or 20 ng/ml IL-4 (R&D Systems, Germany) was added. On day 7 immature DCs were activated with 10 ng/ml TNF-α (R&D Systems, Germany) and 20 µg/ml poly(IC) (Sigma Aldrich, Germany) or 100 ng/ml LPS for 24 hours. Remaining PBMCs and obtained PBLs were aliquoted and frozen.

In Vitro Priming of Specific T Cells

To generate CD4+ T cells, 3 Million PBMCs/PBLs were stimulated with $2 \times 10^5$ autoguous DCs. DCs were harvested on day 8 (see chapter 3.1, Generation of DCs). PBS with 5 mM EDTA was used for this purpose in order to gain as many cells as possible (including adherent cells). After being washed with DC medium, cell number was determined. For loading with peptide, DCs were resuspended in 1 ml DC medium and incubated with 25 µg/ml peptide for 2 hours at 37° C. Peptides used for pulsing of DCs were TGFBI-004, Posmix (mix of EBV and CMV related peptides), Padre and CMV. Autologous PBMCs/PBLs were thawed, washed with DC medium (at least twice) and plated in a 24 well plate at a density of 3 Million cells/ml in 1 ml. DCs loaded with peptide were then added (as 1 ml suspension containing the peptide) to the plated PBMCs/PBLs and incubated for 7 days at 37° C. After priming, obtained CTLs were first restimulated with cryopreserved autologous peptide-loaded PBMCs which have been irradiated (30 Gy; Gammacell 1000 Elite, Nordion International, Canada). $5 \times 10^5$ CTLs and $2.5 \times 10^6$ PBMCs were added per well for this purpose. Pulsing of PBMCs with peptide was performed as aforementioned (for DCs). On day 1 after the first restimulation, IL-2 (R&D Systems, Germany) and IL-7 was added to a final concentration of 2 ng/ml and 5 ng/ml, respectively. Afterwards, every 2nd day and every 7th day, IL-2 and IL-7 were added to the media. Second restimulation was performed 7 days later, but this time peptide was added alone (without PBMCs) to the cultured CTLs. Restimulations were performed in a 7 day cycle, with peptide-loaded PBMCs and peptide alone being added alternatively. Analyses were performed after the eight stimulation by intracellular IFNγ staining and IFNγ ELISPOT.

Results

Figure 6:
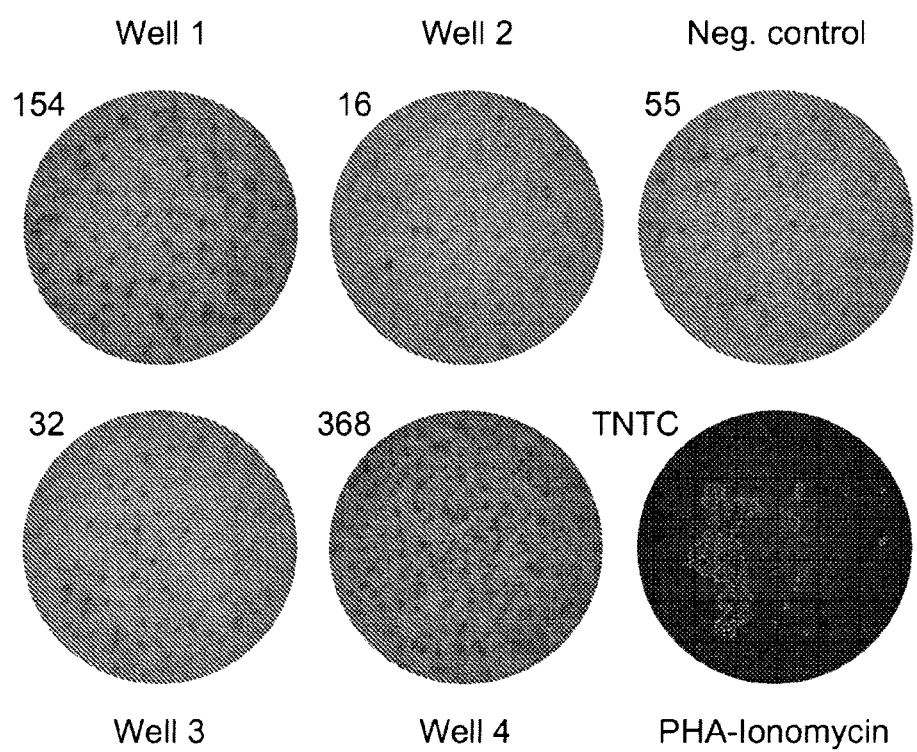
FIG. 6 depicts the in vitro immunogenicity of TGFBI-004 as detected by IFNγ ELISPOT after five stimulation cycles.

It was possible to prime CD4+ T cell lines specifically reacting to the peptide of interest (FIG. 6 and FIG. 3). T-cell responses could be detected via ELISPOT in 2 out of 4 T-cell lines, whereas in 3 out of 4 T-cell lines, TGFBI-004 specific IFNγ producing CD4+ and/or CD8+ cells were shown via ICS.

Thus, TGFBI-004 was able to elicit CD4+ and CD8+ T cell responses in one donor tested with the above described experimental system. According to this promising result, it is likely that this peptide is immunogenic and has the capacity to induce T-cell responses.

Functional Validation Exemplified by NOX-001 and TGFBI-001

Immunogenicity of peptides included in IMA910 vaccine was demonstrated in vitro by using immatics' TUMAP validation platform. The induction of specific T cells is an indication for the ability of peptides to successfully activate the immune system. Since efficient anti-tumor immune response is only possible when activated T cells are of high avidity and functional, the TUMAPs' ability to prime high avidity, functional T lymphocytes was investigated by testing their ability to produce IFNγ or to kill tumor cell lines. Two peptides, NOX-001 and TGFBI-001, were chosen for deeper validation due to their capacity to induce high avidity CTLs in vitro. The results proved that high avidity precursor T cells exist against both peptides in humans and that functional CD8+ T cell lines could be generated by NOX-001.

Principle of Test

To get additional insight on the immunogenicity of IMA910 peptides and the properties of specific T cells, two peptides, NOX-001 and TGFBI-001, were selected for further evaluation. The experiments performed for this purpose were conducted at immatics (cell sorting was performed at the University of Tubingen, lab of Dr. Baring).

Dependent on their ability to be activated by high- or low-density antigen, T cell lines can be divided into high- or low-avidity. As it has been shown before (Walter, S, et al., 2003, J. Immunol., 171, 4974-4978), human high-avidity CTLs can be raised successfully by using less peptide for activation compared to low-avidity CD8+ T cells. It has also been demonstrated that cells expanded this way are more efficient in recognizing antigen-expressing tumor cell lines, hereby constituting a possible major tool in the development of therapy strategies.

To determine the ability of peptides to generate high-avidity CTL lines, isolated human CD8+ cells were primed and expanded by repeated in vitro stimulations with beads coated with low-density pMHC (peptide-MHC-complex) and anti-CD28 antibody in the presence of IL-12 and IL-2. After three stimulations, a fraction of in vitro primed T cells were pMHC-tetramer stained and detected by cytometric analysis. Tetramer-positive cells of each donor were pooled afterwards according to the antigen specificity, stained with pMHC-tetramer and human anti-CD8-FITC antibody and finally subjected to FACS sorting on a FACSAria. Sorted cells were cultured and expanded in the presence of irradiated feeder cells, cytokines and mitogen. As a read-out for the generation of primed high avidity antigen specific cells, pMHC-tetramer staining was performed. In order to determine their functionality, IFNγ production was assayed by ELISPOT and killing of tumor cell lines was examined using a cytotoxicity assay based on live/dead staining after restimulation of the cells with the corresponding peptide and tumor cell lines.

Generation of Specific CD8+ T-cell Lines

In vitro stimulations using artificial antigen presenting cells (aAPC) loaded with peptide-MHC complex (pMHC) and anti-CD28 antibody were conducted as described above. The only difference to the method described above was the fact that stimulations were performed with beads loaded with 2 ng relevant plus 200 ng irrelevant library (pMHC)MHC (low density beads) instead of 200 ng relevant MHC (high density beads). Thus, predominantly high avidity T cells were generated for deeper validation of peptides. After three stimulations, a fraction of in vitro primed T cells was pMHC-tetramer stained and detected by cytometric analysis. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations). Tetramer-positive cells of each donor were pooled afterwards according to the antigen specificity, stained with the corresponding pMHC-tetramer and human anti-CD8-FITC antibody clone SK1 and finally subjected to FACS sorting on a FACSAria (BD Biosciences, Germany). Sorted cells were cultured in T cell medium (RPMI-Glutamax supplemented with 10% heat inactivated human AB serum, 100 U/ml penicillin, 100 µg/ml streptomycin, 1 mM sodium pyruvate and 20 µg/ml Gentamycin) in the presence of $5\times10^5$ cells/ml irradiated fresh allogeneic PBMCs, $5\times10^4$ cells/ml irradiated LG2-EBV cells, 150 U/ml IL-2 (Chiron, Munich, Germany) and 0.5 µg/ml PHA-L (Roche Diagnostics, Mannheim, Germany). Expansion of these cells occurred in T cell medium containing 150 U/ml IL-2. As a read-out for the generation of primed high avidity antigen specific cells, pMHC-tetramer staining was performed as above and analyzed on a four-color FACSCalibur (BD Biosciences, Germany).

Functionality Tests

To determine their functionality, IFNγ production was assessed by ELISPOT (IFNγ ELISPOT Set, BD, Germany) after restimulation of the cells with the corresponding peptide. Additionally, cell-mediated cytotoxicity of specific CTLs was investigated by killing of tumor cell lines using the LIVE/DEAD cell-mediated cytotoxicity Kit (L7010, Invitrogen, Germany). Both assays were performed according to manufacturer's instructions, except noted otherwise.

Results

Both peptides, NOX-001 and TGFBI-001, were immunogenic in vitro as shown by successful priming with low pMHC density aAPCs. For NOX-001 as well as for TGFBI-001 specific T-cell lines could be established by FACS, thus demonstrating that high-avidity CD8+ T cell precursors exist in healthy donors.

Additionally, for NOX-001, one T-cell line could be established that also proved to be functional by ELISPOT since it was specifically expressing IFNγ after restimulation with this peptide (FIG. 8).

Example 7

Synthesis of a Vaccine Comprising Some of the Peptides of the Present Invention

Synthesis and Structure

Peptides were synthesized by standard and well-established solid phase synthesis using Fmoc chemistry. After purification by preparative HPLC, ion-exchange procedure was performed to incorporate physiological compatible counter ions (acetate or chloride). Finally, white to off white solids were obtained after lyophilization. All TUMAPs are administered as acetate salts except IMA-CCN-001 which is supplied as chloride salt for technical reasons during the manufacturing procedure.

Importantly, identity and purity of the peptides can be determined easily and with high accuracy using mass spectrometry, amino acid analysis and analytical HPLC. According to analytical results, all peptides used for IMA910 vaccine show the correct structure with purities≥95%.

TABLE 5

Physico-chemical characteristics of peptides in vaccine IMA910

| No. | Peptide ID | Peptide length (no of amino acids) | Salt form | Physical form | Hygro-scopicity |
|---|---|---|---|---|---|
| 1 | IMA-C20-001 | 9 | Acetate | White to off-white powder | Stored as freeze dried powder. Lyophilized peptides generally have hygro-scopic properties. |
| 2 | IMA-CCN-001 | 9 | Chloride | | |
| 3 | IMA-CEA-004 | 9 | Acetate | | |
| 4 | IMA-CEA-006 | 16 | Acetate | | |
| 5 | IMA-HBV-001 | 10 | Acetate | | |
| 6 | IMA-MET-001 | 9 | Acetate | | |
| 7 | IMA-MMP-001 | 16 | Acetate | | |
| 8 | IMA-MUC-001 | 9 | Acetate | | |
| 9 | IMA-NOX-001 | 9 | Acetate | | |
| 10 | IMA-ODC-001 | 9 | Acetate | | |
| 11 | IMA-PCN-001 | 10 | Acetate | | |
| 12 | IMA-TGFBI-001 | 10 | Acetate | | |
| 13 | IMA-TGFBI-004 | 15 | Acetate | | |
| 14 | IMA-TOP-001 | 10 | Acetate | | |

Particle size distribution and particle shape measurement of the particles obtained after reconstitution have been performed by capturing direct images of each individual particle in the range of 0.25 to 100 µm followed by image analysis. As a result the majority (>95%) of the particles have been found in the range of 0.25 to 2.7 µm. So far, no major differences in size and shape distribution could be observed within 1, 2 or 3 hours after reconstitution.

Furthermore, analytical HPLC was performed for a closer characterization of the obtained suspension. It could be demonstrated that the particles consist mainly of two peptides (IMA-TGFBI-001 and IMA-NOX-001) which are almost insoluble in the solution used for reconstitution of IMA910. Additionally, low amounts of 4 other peptides (IMA-CEA-006, IMA-TOP-001, IMA-CCN-001 and IMA-HBV-001) were also found in the particles. The composition of the particles (qualitatively and quantitatively) was found to be very similar in two independently manufactured batches.

Mannitol and Polysorbate 80 (Tween 80) have been used as excipients and non-active ingredients to improve solubility characteristics of the peptide lyophilisate.

IMA910 is dissolved in 700 μL sodium hydrogen carbonate (4.2%).

To reconstitute IMA910, 700 μL of the diluent is injected through the stopper into the vial by a 1 mL syringe equipped with a needle. To dissolve IMA910, the vial and the diluent shall be shaken gently for about 2 minutes. Shaking should be performed carefully in order to avoid strong foaming. By this procedure a white to off-white homogeneous suspension will be obtained. To avoid any sedimentation the vial content shall be gently shaken before transferring 500 μL of this suspension into a new syringe equipped with a needle (size: G20). 10 to 30 minutes after GM-CSF injection administer 500 μL reconstituted IMA910 i.d. at the same injection site. Administration has to occur within 1 h after reconstitution. Dissolved lyophilisate may be stored aseptically at room temperature for up to 1 hour following reconstitution.

IMA910 is composed of a cocktail of 13 synthetic tumor-associated peptides (TUMAPs) of which the majority has been identified on primary colorectal carcinoma (CRC) cells. The TUMAPs include 10 HLA class I-binding peptides with the capacity to activate cytotoxic T cells (CD8+ T cells) and 3 HLA class II-binding peptides with the capacity to activate T helper cells (CD4+ T cells). In addition to these 13 TUMAPs IMA910 contains one control peptide of viral origin.

Example 8

Binding of HLA Class I-restricted Peptides of the Invention to HLA-A*0201

The objective of this analysis was to evaluate the affinity of the HLA class I peptides CHI-001, DCA-001, JAK-001 and PTP-001 to the MHC molecule coded by the HLA-A*0201 allele. Affinities for all peptides to HLA-A*0201 were comparable to the well-known control peptide HBV-001, dissociations constants ($K_D$) being in the range from 0.05 to 1.6 nM.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules." When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester-Hvid C, et al., (2002) Tissue Antigens 59, 251-258).

Purified recombinant HLA-A*0201 molecules were incubated together with b2m and graded doses of the peptide of interest. The amount of de novo-folded HLA/peptide complexes was determined by a quantitative ELISA. Dissociation constants ($K_D$ values) were calculated using a standard curve recorded from dilutions of a calibrant HLA/peptide complex.

Results

Results are shown in FIG. 9 A lower $K_D$ value reflects higher affinity to HLA-A*0201. Affinities for all peptides to HLA-A*0201 were comparable to the well-known control peptide HBV-001, dissociations constants ($K_D$) being in the range from 0.05 to 1.6 nM.

The invention claimed is:

1. An isolated peptide comprising SEQ ID No. 2, wherein said peptide has an overall length of not more than 100 amino acids, or a pharmaceutically acceptable salt thereof.

2. The peptide according to claim 1, wherein said peptide has an overall length of from 8 to 30 amino acids.

3. An isolated peptide having an overall length of not more than 30 amino acids, wherein said peptide comprises a variant of SEQ ID NO: 2, wherein said variant of SEQ ID No. 2 is modified in that at least one side chain of one or two amino acid residues are altered and wherein the peptide and/or variant is able to bind to an HLA molecule in substantially the same way as a peptide consisting of the amino acid sequence of SEQ ID No. 2, or a pharmaceutically acceptable salt thereof.

4. The peptide according to claim 1, wherein the peptide consists of an amino acid sequence according to SEQ ID No. 2.

5. The peptide according to claim 1, wherein said peptide includes non-peptide bonds.

6. A fusion protein, comprising SEQ ID NO: 2 and N-terminal amino acids of the HLA-DR antigen-associated invariant chain (Ii), or a pharmaceutically acceptable salt thereof.

7. A method of producing a peptide and/or variant according to claim 1, the method comprising culturing a host cell and isolating the peptide from the host cell and/or a culture medium thereof.

8. An in vitro method for producing activated cytotoxic T lymphocytes (CTL), the method comprising contacting in vitro CTL with antigen loaded human class I or II MHC molecules expressed on a surface of an antigen-presenting cell for a period of time sufficient to activate said CTL in an antigen specific manner, wherein said antigen is a peptide according to claim 1.

9. The method according to claim 8, wherein the antigen is loaded onto a class I or II MHC molecule expressed on a surface of an antigen-presenting cell by contacting said antigen with said antigen-presenting cell.

10. The method according to claim 8, wherein the antigen-presenting cell comprises an expression vector.

11. A medicament for inducing an immune response in a subject, said medicament comprising a peptide of claim 1, or a pharmaceutically acceptable salt thereof.

12. A medicament according to claim 11, wherein the medicament is a vaccine.

13. A medicament according to claim 11, wherein the medicament is active against cancer cells.

14. A medicament according to claim 13, wherein said cancer cells comprise glioblastoma cells, colorectal, pancreatic, lung, renal or gastric cancer cells.

* * * * *